(12) United States Patent
Song

(10) Patent No.: US 8,124,757 B2
(45) Date of Patent: Feb. 28, 2012

(54) THIOL-MODIFIED MACROMOLECULE DERIVATIVES AND CROSS-LINKED MATERIALS THEREOF

(75) Inventor: Chan Song, Shanghai (CN)

(73) Assignee: Bioregen Biomedical (Changzhou) Co., Ltd., Changzhou (CN)

( * ) Notice: Subject to any disclaimer, the term of this patent is extended or adjusted under 35 U.S.C. 154(b) by 442 days.

(21) Appl. No.: 12/518,473

(22) PCT Filed: Sep. 29, 2007

(86) PCT No.: PCT/CN2007/002864
§ 371 (c)(1),
(2), (4) Date: Jun. 10, 2009

(87) PCT Pub. No.: WO2008/071058
PCT Pub. Date: Jun. 19, 2008

(65) Prior Publication Data
US 2010/0152423 A1    Jun. 17, 2010

(30) Foreign Application Priority Data
Dec. 11, 2006    (CN) .......................... 2006 1 0119414

(51) Int. Cl.
C08B 37/08    (2006.01)
C07K 14/78    (2006.01)
(52) U.S. Cl. ......................................... 536/53; 530/354
(58) Field of Classification Search ................. 530/354; 536/53
See application file for complete search history.

(56) References Cited

U.S. PATENT DOCUMENTS
2004/0038934 A1    2/2004    Bulpitt et al.
2005/0176620 A1*    8/2005    Prestwich et al. ................. 514/2
2006/0110458 A1    5/2006    Hahn et al.

FOREIGN PATENT DOCUMENTS
EP        1683812 A1        7/2006
JP        63-57569 A        3/1988
WO        WO 2004/037164 A2    5/2004
WO        WO 2005/056608 A1    6/2005

OTHER PUBLICATIONS

Shu et al., "Disulfide Cross-Linked Hyaluronan Hydrogels," Biomacromolecules, vol. 3, No. 6, Sep. 27, 2002, pp. 1304-1311.
Shu et al., "Disulfide-crosslinked hyaluronan-gelatin hydrogel films: a covalent mimic of the extracellular matrix for in vitro cell growth," Biomaterials, vol. 24, Apr. 8, 2003, pp. 3825-3834.

* cited by examiner

*Primary Examiner* — Shailendra Kumar
(74) *Attorney, Agent, or Firm* — Birch, Stewart, Kolasch & Birch, LLP

(57) ABSTRACT

The disclosed is thiol-modified macromolecule derivatives having the general formula of (I) or (II), as well as the disulfide bond cross-linked materials and the thiol-reactive crosslinker cross-linked materials, wherein $R_1$ and $R_2$ are alkylene groups, substituted alkylene groups, aromatic groups or polyether groups and the like, respectively. $R_1$ and $R_2$ may have same or different chemical structure, and P is a residue of a macromolecule with side carboxyl group. The thiol-modified macromolecule derivative has a molecular weight of from 1000 to 5,000,000. The thiol-modified macromolecule derivative having the general formula of (I) or (II) of the present invention has a side chain with flexible chemical structure and adjustable properties, and has a number of advantages, such as mild reaction condition, high production yield, high degree of modifying, and the controllable modifying degree and so on. The cross-linked material made from the thiol-modified macromolecule derivative of the present invention can be used to inhibit cell attachment and be used as the matrix for cell attachment growth.

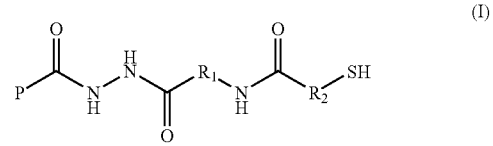

(I)

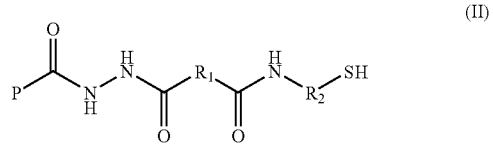

(II)

20 Claims, 2 Drawing Sheets

THIOL-MODIFIED MACROMOLECULE DERIVATIVES AND CROSS-LINKED MATERIALS THEREOF

This application is a 371 of PCT/CN07/02864, filed on Sep. 29, 2007.

TECHNICAL FIELD

The invention relates to compounds, especially to thiol-modified macromolecule derivatives. In addition, it also relates to disulfide bond and thiol-reactive crosslinker cross-linked materials composed of thiol-modified macromolecule derivatives.

BACKGROUND TECHNOLOGY

The thiol-modified macromolecule derivatives have many important uses in biomedicine, such as for chemical-active modification of various small molecular drugs and polypeptide/protein drugs, for preparing various cross-linked macromolecule materials and so on. These new materials can be used as the cell growth matrix, the wound repairing and regenerating matrix, the drug delivery carrier, the wound dressing, in situ cell encapsulation matrix and so on. They play important roles in biomedicine. So far, however, few kinds of thiol-modified macromolecule derivatives are reported. Only the thiol-modified macromolecule derivatives that reported by Shu et al. in *Biomacromolecules,* 3, 1304, 2002 showed good perspective of application and this kind of thiol-modified macromolecule derivative have the following structure:

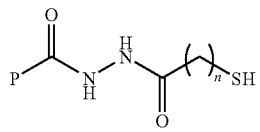

n = 2, 3

Wherein, P is a residue of macromolecule. However the side chain structures and properties of these thiol-modified macromolecule derivatives are unitary and cannot meet the various requirements in biomedicine well. Moreover, the side chains of these thiol-modified macromolecule derivatives are very short, which limits the probability of collision between their thiols and other chemical functional groups when they are modified and cross-linked chemically further, which may lead to the weak chemical reactivity. So, it is of great significance to prepare thiol-modified macromolecule derivatives with adjustable molecular structure of side chain and chemical properties.

CONTENT OF THE INVENTION

One technical problem to be solved in this invention is to provide a new kind of thiol-modified macromolecule derivatives with important biomedical usages which contain adjustable molecular structure of side chain and has adjustable chemical properties.

The second technical problem to be solved of this invention is to provide a kind of disulfide bond cross-linked materials composed of the thiol-modified macromolecule derivatives.

The third technical problem to be solved of this invention is to provide a kind of cross-linked materials composed of thiol-modified macromolecule derivatives and cross-linked by thiol-reactive crosslinker.

Of this invention, the macromolecules with side carboxyl groups are used as starting materials, and the new thiol-modified macromolecule derivatives are synthesized through chemical modification. This kind of derivatives contains adjustable molecular structure of side chain and has adjustable chemical properties, and has important uses in biomedicine.

The thiol-modified macromolecule derivatives in this invention are represented as the following general formula (I) or (II):

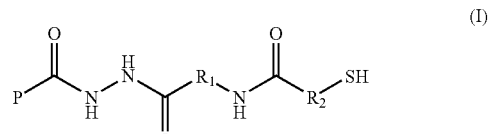

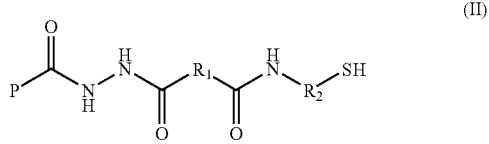

Wherein, $R_1$ and $R_2$ can be an alkylene group, a substituted alkylene group, an arylene group, a polyether backbone etc.; $R_1$ and $R_2$ may have same or different chemical structures; the thiol-modified macromolecule derivatives has the molecular weight from 1000 to 5,000,000.

Above P is a residue of macromolecules with side carboxyl groups, wherein at least one carboxyl group of side chains is modified into thiol. The macromolecules with side carboxyl groups include polysaccharides, proteins, synthesized macromolecules and so on. Wherein, the polysaccharides include chondroitin sulfate, dermatan, heparin, heparan, alginic acid, hyaluronic acid, dermatan sulfate, pectin, carboxymethyl cellulose, carboxymethyl chitosan etc. and their salts; the synthesized macromoleculars include polyacrylic acid, polyaspartic acid, polytartaric acid, polyglutamic acid, polyfumaric acid etc. and their salts; the proteins include collagen protein, alkaline type gelatin, acidic type gelatin, alkaline type gene-recombinated gelatin, acidic type gene-recombinated gelatin, elastin, decorin, laminin, fibronectin etc. The preferred macromolecules with side carboxyl groups include chondroitin sulfate, heparin, heparan, alginic acid, hyaluronic acid, polyaspartic acid, polyglutamic acid and their salts (such as sodium salt, potassium salt etc.), alkaline type gelatin, acidic type gelatin, alkaline type gene-recombinated gelatin, acidic type gene-recombinated gelatin. Wherein, chondroitin sulfate, heparin, hyaluronic acid and their salts (such as sodium salt, potassium salt etc.) and alkaline type gelatin, acidic type gelatin are especially preferred.

The above-mentioned alkylene group refers to —$(CH_2)_n$— (n is an integer from 1 to 15), and the preferred n is an integer from 1 to 8.

The above-mentioned substituted alkylene group refers to the alkylene group whose at least one hydrogen atoms is substituted by lower alkyl, hydroxyl group, amino, alkoxyl, phenyl, and ester group etc.

The above-mentioned arylene group refers to phenylene group, naphthylene group etc., and preferably to phenylene group.

The above-mentioned polyether backbone refers to group of —$[(CHR)_nO]_m$—, wherein, R is a lower alkyl, n is an integer from 1 to 10, m is an integer from 1 to 500. The preferred R is a hydrogen atom, while n equals to 2, 3 or 4.

The above-mentioned lower alkyl refers to those straight-chain or branched-chain alkyl groups having 1~8 carbon atoms e.g. methyl, ethyl, propyl, isopropyl, butyl, isobutyl, tert-butyl, sec-butyl, amyl, neopentyl, hexyl, heptyl, octyl etc. The straight-chain or branched-chain alkyls having 1-4 carbon atoms, and especially methyl, ethyl and propyl are preferred.

The above-mentioned alkoxyl refers to straight-chain or branched-chain alkoxyl groups having 1-6 carbon atoms e.g. methoxyl, ethoxyl, propoxyl, iso-propoxyl, butoxyl, isobutoxyl, tert-butoxyl, sec-butoxyl, pentoxyl, neopentoxyl, hexoxyl and so on. The straight-chain or branched-chain alkoxyl groups having 1-4 carbon atoms, and especially methoxyl and ethoxyl are preferred.

The above mentioned ester group refers to —C(O)OR, wherein R is the above-mentioned lower alkyl, and preferably to methoxycarbonyl, ethoxycarbonyl, propoxycarbonyl and butoxycarbonyl.

The preferred compounds of this invention are those whose $R_1$ and $R_2$ is an alkylene group respectively. The most preferred compounds are those whose $R_1$ and $R_2$ is an alkylene group having 1~8 carbon atoms respectively.

For example, if P is a residue of hyaluronic acid, the thiol-modified macromolecule derivatives in this invention have the following chemical structure feature:

Wherein, $R_1$ and $R_2$ are defined as above; i is an integer greater than 0; j is an integer equal to or greater than 0.

The thiol-modified macromolecule derivatives with general formula (I) or (II) of this invention are normally prepared through hydrazide/carbodiimide coupling chemical method. The basic principle is as follows: firstly the side carboxyl groups of macromolecules are activated by carbodiimide to form a reactive intermediate, then the reactive intermediate is attacked nucleophilically by the amino of dihydrazide having a disulfide linkage to form an adduct, lastly the disulfide bonds of the adduct is deoxidized to free thiols and the product is collected after purification.

In order to prepare the thiol-modified macromolecule derivatives with general formula (I) or (II) of this invention, the following two kinds of new dihydrazides having a disulfide linkage should be synthesized firstly according to the invention patent applied by the same applicant of this invention (Application Number: 200610118715.2; Invention title: Dihydrazide compounds, preparation and uses thereof):

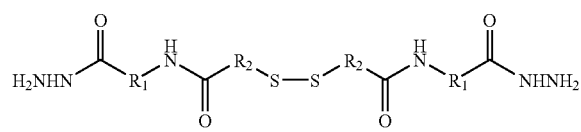

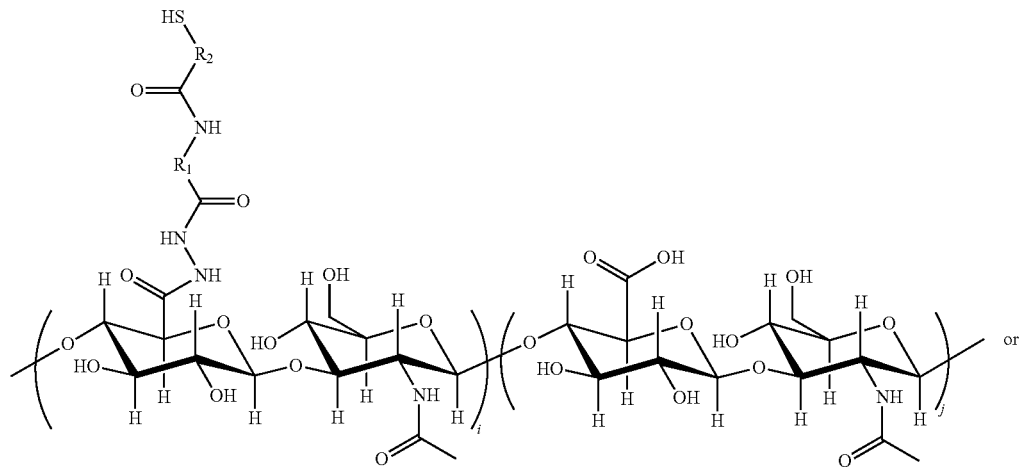

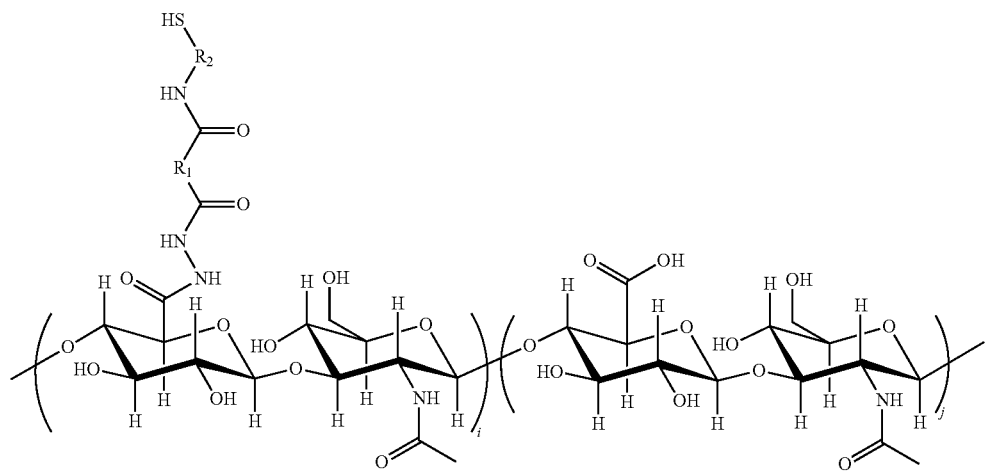

-continued

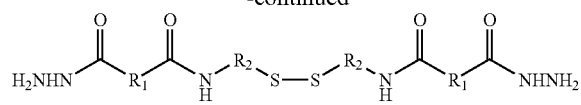

Wherein, $R_1$ and $R_2$ are defined as previously. These two kinds of new dihydrazides having a disulfide linkage, characterized by a disulfide bond, two amide bonds and two hydrazide functional groups, can be prepared from corresponding dicarboxylic acids having a disulfide linkage or diamines having a disulfide linkage. The followings are the chemical structures of some dihydrazides having a disulfide linkage which can be used to prepare the thiol-modified macromolecule derivatives with general formula (I) or (II) of this invention:

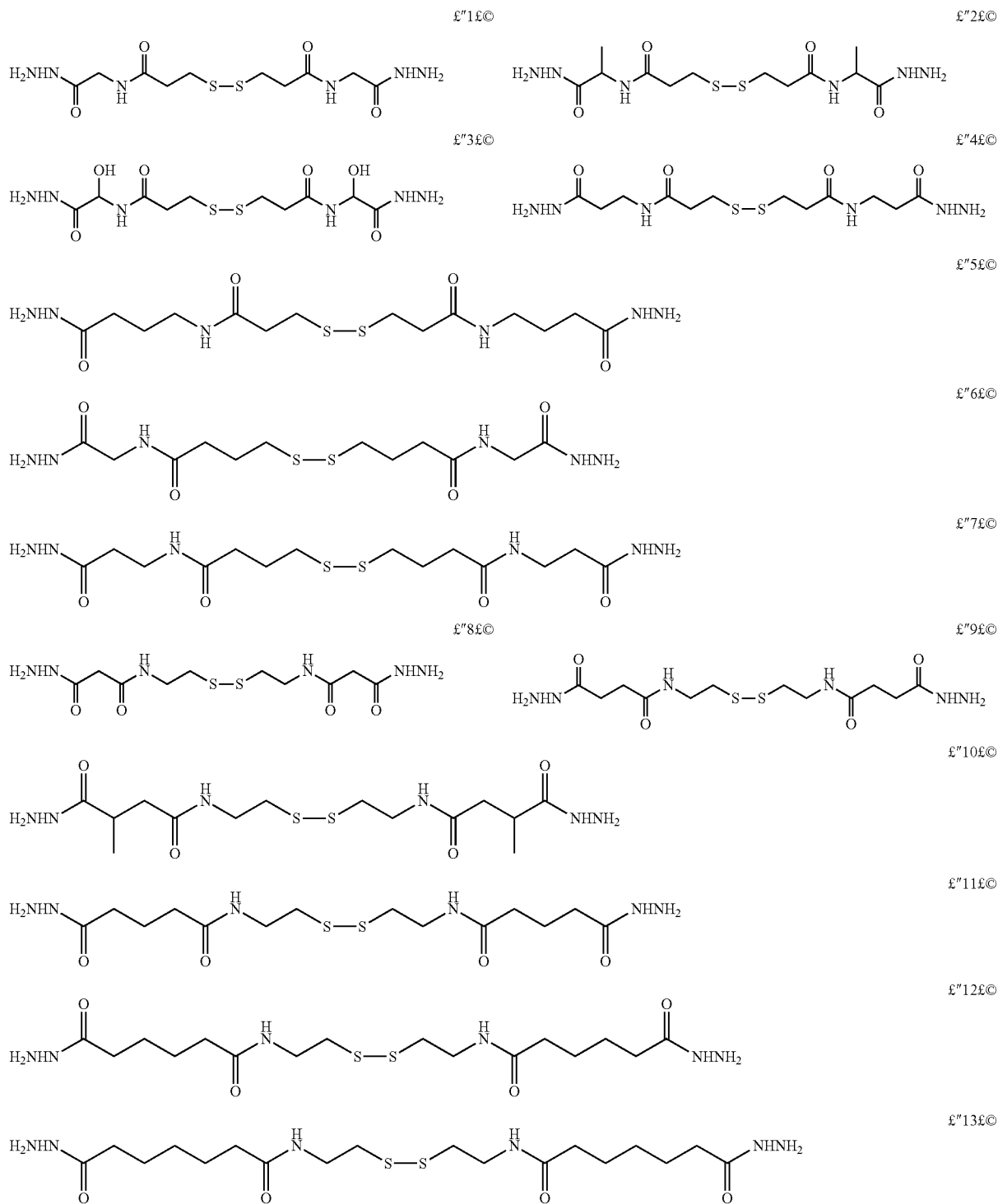

Wherein, compound (1) is dithiodiethanediyldicarbonyldiamino diacetic acid dihydrazide (abbr. DGDTPDH); compound (2) is dithiodiethanediyldicarbonyldiamino dimethylacetic acid dihydrazide (abbr. DADTPDH); compound (3) is dithiodiethanediyldicarbonyldiamino dihydroxylacetic acid dihydrazide (abbr. DHADTPDH); compound (4) is dithiodiethanediyldicarbonyldiamino dipropionic acid dihydrazide (abbr. DPDTPDH); compound (5) is dithiodiethanediyldicarbonyldiamino dibutanoic acid dihydrazide (abbr. DBDTPDH); compound (6) is dithiodipropanediyldicarbonyldiamino diacetic acid dihydrazide (abbr. DGDTBDH); compound (7) is dithiodipropanediyldicarbonyldiamino dipropionic acid dihydrazide (abbr. DPDTBDH); compound (8) is dithiodiethanediyldiaminodicarbonyl diacetic acid dihydrazide (abbr. DPCDH); compound (9) is dithiodiethanediyldiaminodicarbonyl dipropionic acid dihydrazide (abbr. DSCDH); compound (10) is dithiodiethanediyldiaminodicarbonyl diisobutanoic acid dihydrazide (abbr. DMPCDH); compound (11) is dithiodiethanediyldiaminodicarbonyl dibutanoic acid dihydrazide (abbr. DGCDH); compound (12) is dithiodiethanediyldiaminodicarbonyl dipentanoic acid dihydrazide (abbr. DACDH); and compound (13) is dithiodiethanediyldiaminodicarbonyl dihexanoic acid dihydrazide (abbr. DHCDH).

A method for preparing the thiol-modified macromolecule derivatives with general formula (I) or (II) of this invention is as follows: after activated by 1-ethyl-3-(3-dimethylaminopropyl)carbodiimide hydrochloride, the side carboxyl groups of macromolecule reacts with one or two hydrazide functional groups of dihydrazide having a disulfide linkage to form an adduct; then the disulfide bonds of the adduct are deoxidized to free thiols by mercaptan alcohol, dithiothreitol, sodium borohydride or other deoxidizers, at last the thiol-modified macromolecule derivatives with general formula (I) or (II) of this invention is collected after dialysis purification to remove the impurities. The followings are the chemical synthesis pathway and chemical structures, wherein, $R_1$ and $R_2$ can be an alkylene group, a substituted alkylene group, an arylene group, a polyether backbone etc.

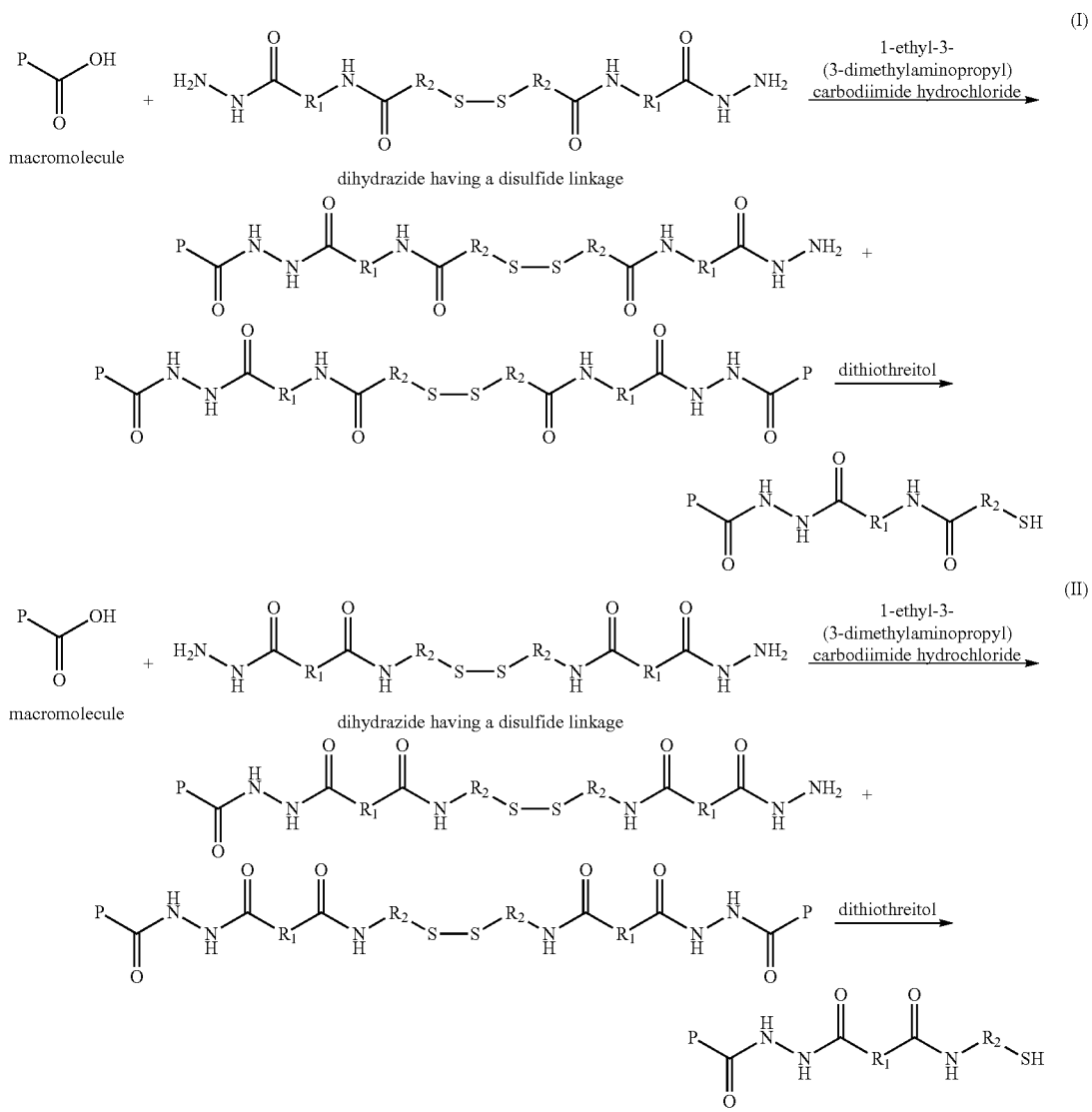

The preferred thiol-modified macromolecule derivatives with general formula (I) or (II) of this invention are those whose $R_1$ and $R_2$ is an alkylene group respectively and the followings are their chemical structures:

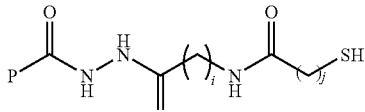

(1)

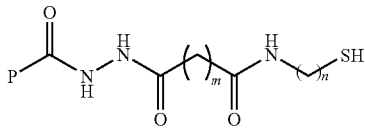

(2)

Wherein, formula (I) represents the general chemical structure of the thiol-modified macromolecule derivatives with general formula (I) or (II) that $R_1$ and $R_2$ are an alkylene group respectively; formula (2) represents the general chemical structure of thiol-modified macromolecule derivatives with general formula (I) or (II) that $R_1$ and $R_2$ are an alkylene group respectively (i, j, m, n are an integer greater than 1).

The most preferred thiol-modified macromolecule derivatives with general formula (I) or (II) of this invention are those whose $R_2$ is an alkylene group having 2 or 3 carbon atoms and $R_1$ is an alkylene group having 1~5 carbon atoms and P is the residue of one of chondroitin sulfate, heparin, an hyaluronic acid and their salts (such as sodium salt, potassium salt etc.), or alkaline type gelatin, acidic type gelatin. The followings are their chemical structures:

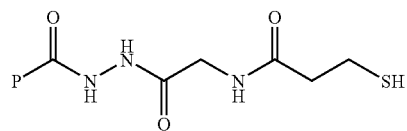

(1)

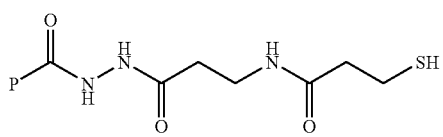

(2)

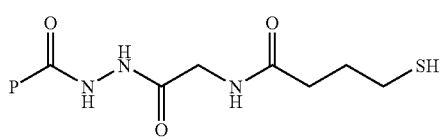

(3)

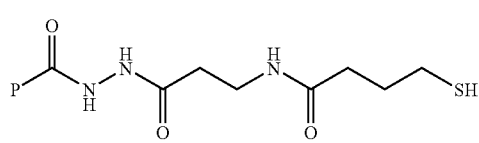

(4)

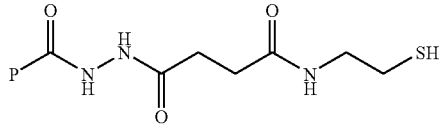

(5)

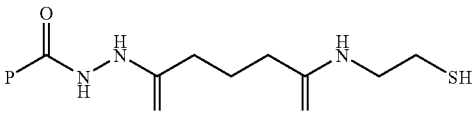

(6)

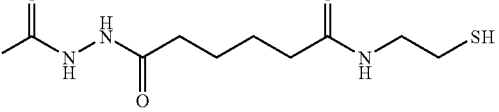

(7)

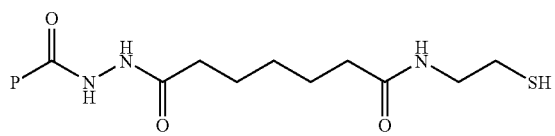

(8)

Wherein, compound (1) is the thiol-modified macromolecule derivatives modified by dithiodiethanediyldicarbonyldiamino diacetic acid dihydrazide (abbr. P-DGDTPDH); compound (2) is the thiol-modified macromolecule derivatives modified by is dithiodiethanediyldicarbonyldiamino dipropionic acid dihydrazide (abbr. P-DPDTPDH); compound (3) is the thiol-modified macromolecule derivatives modified by dithiodipropanediyldicarbonyldiamino diacetic acid dihydrazide (abbr. P-DGDTBDH); compound (4) is the thiol-modified macromolecule derivatives modified by dithiodipropanediyldicarbonyldiamino dipropionic acid dihydrazide (abbr. P-DADTBDH); compound (5) is the thiol-modified macromolecule derivatives modified by dithiodiethanediyldiaminodicarbonyl dipropionic acid dihydrazide (abbr. P-DSCDH); compound (6) is the thiol-modified macromolecule derivatives modified by dithiodiethanediyldiaminodicarbonyl dibutanoic acid dihydrazide (abbr. P-DGCDH); compound (7) is the thiol-modified macromolecule derivatives modified by dithiodiethanediyldiaminodicarbonyl dipentanoic acid dihydrazide (abbr. P-DACDH); and compound (8) is the thiol-modified macromolecule derivatives modified by dithiodiethanediyldiaminodicarbonyl dihexanoic acid dihydrazide (abbr. P-DHCDH).

The molecular weight and its distribution do not change remarkably during thiol-modification. Generally, the molecular weight and its distribution of thiol-modified macromolecule derivatives with general formula (I) or (II) of this invention are almost the same as those of the starting materials (macromolecules with side carboxyl groups). Various starting materials (macromolecule with side carboxyl groups) have rather different molecular weight generally from 1000 to 5,000,000 and have also rather different molecular weight distribution. For example, generally, the molecular weight distribution of gelatin is broad. The molecular weight and its distribution of the starting materials (macromolecules with side carboxyl groups) do not affect the process of thiol-modification and do not affect the preparation of thiol-modified macromolecule derivatives with general formula (I) or (II) of this invention.

The thiol-modified macromolecule derivatives with general formula (I) or (II) of this invention has many beneficial effects. The use of hydrazide coupling method for thiol-modification of this invention has the notable benefits: mild preparing conditions, high rate of production, high degree of modification, good controllability and so on. Compared with the side chain of thiol-modified macromolecule derivatives reported in *Biomacromolecules*, 3, 1304, 2002 and WO 2004/03716 by Shu et al., the side chain of thiol-modified macromolecule derivatives with general formula (I) or (II) of this invention has more flexible chemical structures and more adjustable characters due to the introduction of an amide bond creatively, despite that the hydrazide coupling method is used for thiol-modification both. Related studies indicate that the thiol-modified macromolecule derivatives with general formula (I) or (II) in this invention have two following major favorable effects:

(1) By the introduction of amide bond, the length and structure of side chains can be adjusted flexibly. The length of side chains impacts greatly on the reactivity of thiols (Shu et al., *Biomaterials* 24, 3825, 2003). The longer the side chain is, the higher the probability of collision between the terminal thiols and other reactive functional groups is. So the reactivity is improved greatly further.

(2) The amide bond is a highly electrophilic group. The introduction of amide bond to the side chain of compound of this invention impacts greatly on the ionization constant (pKa) of terminal thiols, but it depends on the linkage mode of amide bond. In the thiol-modified macromolecule derivatives with general formula (I) of this invention, the carbonyl of amide bond of side chain is close to the terminal thiol, which strengthens the ionization of terminal thiols (pKa decreases); on the contrary, for the thiol-modified macromolecule derivatives with general formula (II) of this invention, the nitrogen atom of amide bond of side chain is close to the terminal thiols, which weakens the ionization of terminal thiols (pKa increases). Generally, compared with the thiol-modified derivatives of whose linkage segment of the side chain is an alkylene group (having 2 or 3 carbon atoms), which is discovered in *Biomacromolecules*, 3, 1304, 2002 and WO 2004/03716 by Shu et al., the ionization constant (pKa) of thiols of thiol-modified macromolecule derivatives with general formula (I) of this invention decreases by about 0.1~0.4, and the ionization constant (pKa) of thiols of thiol-modified macromolecule derivatives with general formula (II) of this invention increases by about 0.2~0.7. Thus the terminal thiols of thiol-modified macromolecule derivatives with general formula (I) in this invention is more active, and the terminal thiols of thiol-modified macromolecule derivatives with general formula (II) in this invention is more stable.

Compared with the thiol-modified derivatives of which have been reported, the thiol-modified macromolecule derivatives with general formula (I) or (II) of this invention have much more particular characters. The compounds of appropriate chemical structure can be chosen according to the acquirement of practical application. The following thiol-modified derivatives of hyaluronic acid (HA) are taken as examples to describe the favorable effects of thiol-modified macromolecule derivatives with general formula (I) or (II) of this invention further:

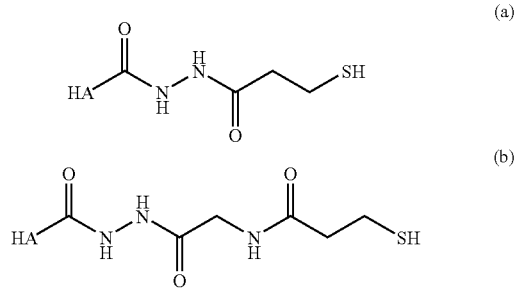

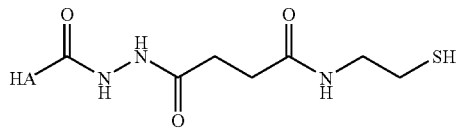

The above compounds have the same structures of terminal thiol segment. Wherein, compound (a) is the thiolated derivatives of macromolecule reported in *Biomacromolecules*, 3, 1304, 2002 and WO 2004/03716 by Shu et al.; compound (b) is the thiol-modified macromolecule derivatives with general formula (I) of this invention; compound (c) is the thiol-modified macromolecule derivatives with general formula (II) of this invention. The reaction ability of thiol-modified macromolecule derivatives (b) is far more active than that of compound (a), and its ability of forming disulfide-bond-cross-linked gel increases by about 50%. The reaction ability of thiol-modified macromolecule derivatives (c) is far more inactive than that of compound (a), and the stability of its thiol increases by more than one time.

The thiol-modified macromolecule derivatives with general formula (I) or (II) of this invention contains at least one side free thiol, and can be oxidated to form a disulfide bond again under proper conditions. Oxygen, low concentration hydrogen peroxide, iodine, trivalent ferric ion and other moderate oxidizers can enable the free thiol to form a disulfide bond, thus the cross-linked macromolecule materials is prepared. The formation of disulfide bond generally depends on pH value of the solution: under alkaline conditions, the thiol ionizes to negative ion which has highly activity and even the oxygen in the air can promote the formation of disulfide bond rapidly; however, under acidic conditions, the ionization of thiol is inhibited and the reactivity decreases and the thiol is more stable. The thiol of thiol-modified macromolecule derivatives with general formula (I) of this invention is more active and can form a disulfide-bond cross-linked material even under the neutral conditions or under the action of weak oxidizers. However, the thiols of thiol-modified macromolecule derivatives with general formula (II) of this invention is more stable and forms a disulfide-bond cross-linked material rapidly only under the alkalescent conditions or under the action of strong oxidizers.

The method for preparing disulfide-bond cross-linked materials composed of thiol-modified macromolecule derivatives of this invention is simple and dependable and the product is flexible. The usual preparing method is as follows: prepare the aqueous solution or mixed aqueous solution of the thiol-modified macromolecule derivatives with general formula (I) or (II) of this invention and prepare the disulfide-bond cross-linked materials through the oxidation of oxygen in the air under the neutral or alkalescent conditions at room temperature; or prepare the disulfide-bond cross-linked materials through the oxidation of low concentration hydrogen peroxide, trivalent ferric ion and other stronger oxidizers under the acidulous or acidic conditions.

The disulfide cross-linked materials composed of one or two thiol-modified macromolecule derivatives of this invention are represented as the following general formula (III), (IV) or (V):

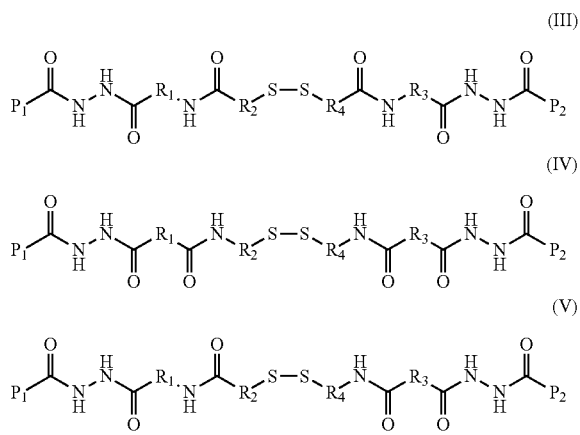

Wherein, $P_1$ and $P_2$ are the residue of macromolecules with side carboxyl groups defined as previously; $R_5$ and $R_4$ are defined the same as $R_1$ and $R_2$; $R_1$, $R_2$, $R_5$ and $R_4$ may have same or different chemical structures. It is the single-component cross-linked material while $P_1$ is the same as $P_2$ and it is the two-component cross-linked material while $P_1$ is not the same as $P_2$.

The disulfide cross-linked materials composed of three or more thiol-modified macromolecule derivatives of this invention, whose structure is characterized by formation of disulfide bond by linking three or more macromolecule compounds, are prepared using three or more thiol-modified macromolecule derivatives of general formula (I) or (II).

The cross-linked materials composed of the thiol-modified macromolecule derivatives of this invention and cross-linked by thiol-reactive crosslinker, are prepared using one or more thiol-modified macromolecule derivatives with general formula (I) or (II) and thiol-reactive crosslinker. The thiol-reactive functional group used in this invention includes maleimide, vinyl sulfone, α, β unsaturated acrylic acid ester, α, β unsaturated methacrylic acid ester, halogenated propionic acid ester, halogenated propionamide, dipyridyl disulfide, N-hydroxysuccinimide ester and so on. Wherein, maleimide, vinyl sulfone, iodopropionic acid ester, iodopropionamide, dipyridyl disulfide etc have high thiol-reactivity. The thiol-modified macromolecule derivatives with general formula (I) in this invention is taken as an example to illustrate the chemical equation between thiols and these functional groups as follows, wherein, $R_1$ and $R_2$ can be an alkylene group, a substituted alkylene group, an arylene group, or a polyether backbone etc.

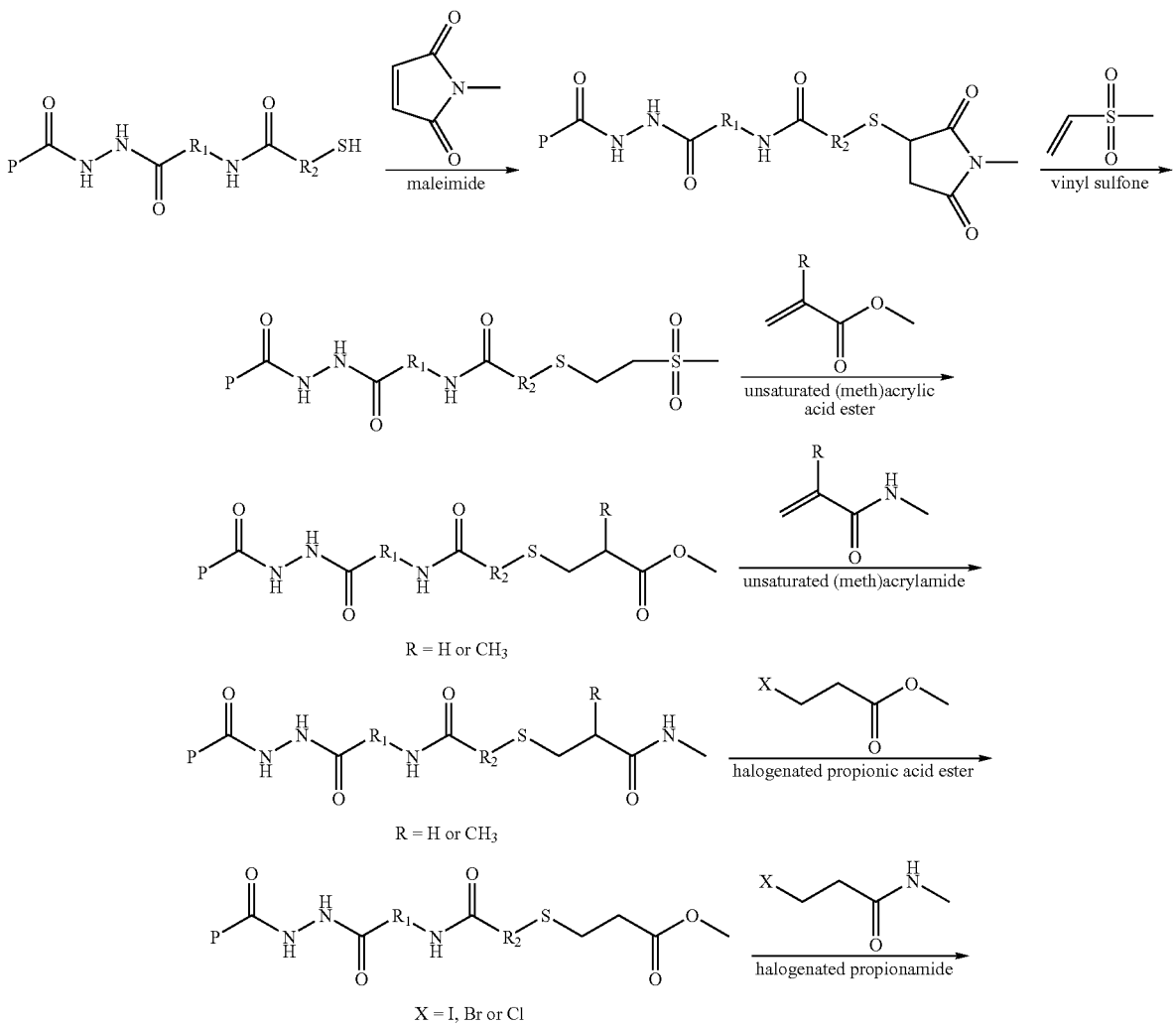

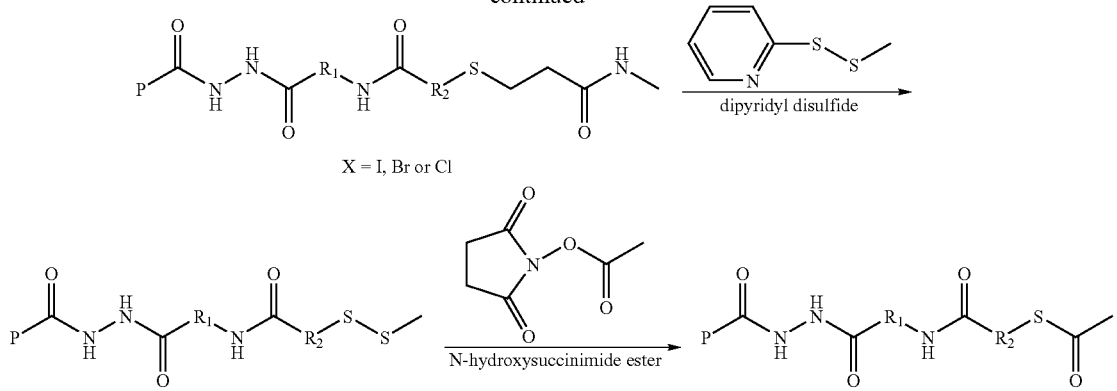

X = I, Br or Cl

These reactions include three kinds: (1) addition reaction between thiol and activated unsaturated double bond. The functional group which can be used in this kind of reactions includes maleimide, vinyl sulfone, α, β unsaturated acrylic acid ester, α, β unsaturated methacrylic acid ester and so on; (2) substitution reaction between thiol and activated alkylogen. The functional group which can be used in this kind of reactions includes iodopropionic acid ester, bromated propionic acid ester, chloropropionic acid ester, iodopropionamide, bromated propionamide, chloropropionamide, dipyridyl disulfide and so on; (3) the last kind is thioesterification reaction. The functional group which can be used in this kind of reactions includes activated esters of various carboxylic acids, such as N-hydroxysuccinimide ester and so on.

The thiol-reactive crosslinker used in this invention is the derivative of polyethylene glycol (abbr. PEG) having at least two above-mentioned reaction functional groups, such as two-arm, three-arm, four-arm, eight-arm and more arms PEG derivatives having the following typical chemical structures:

Taken two-arm PEG as an example, the following is the chemical structure of common crosslinker (two-arm PEG thiol-reactive crosslinker) used in this invention.

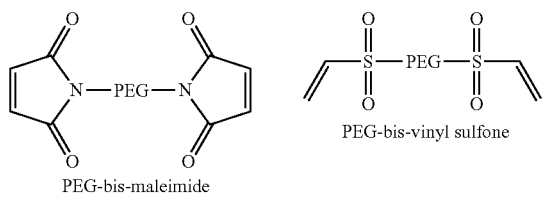

PEG-bis-maleimide          PEG-bis-vinyl sulfone

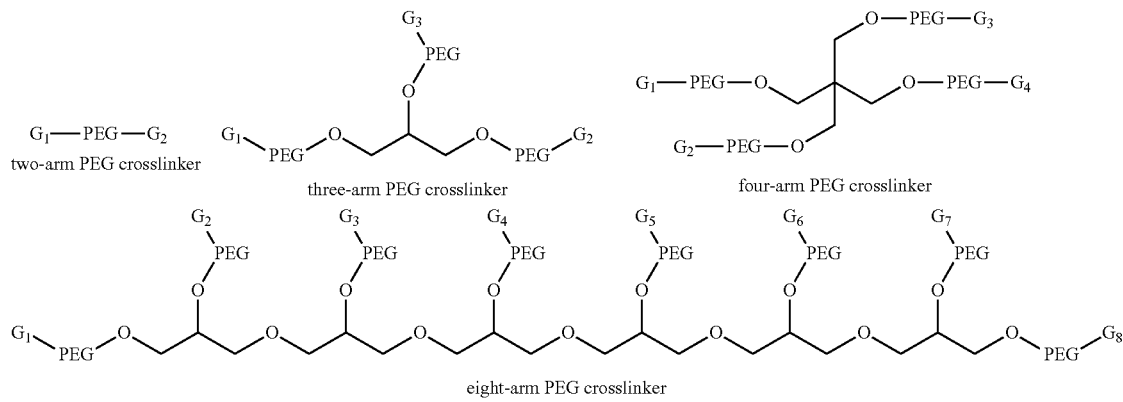

G₁—PEG—G₂
two-arm PEG crosslinker three-arm PEG crosslinker four-arm PEG crosslinker eight-arm PEG crosslinker Wherein, $G_1$, $G_2$, $G_3$, $G_4$, $G_5$, $G_6$, $G_7$ and $G_8$ are above-mentioned thiol-reactive functional groups e.g. maleimide, vinyl sulfone, α, β unsaturated acrylic acid ester, α, β unsaturated methacrylic acid ester, halogenated propionic acid ester, halogenated propionamide, dipyridyl disulfide, N-hydroxysuccinimide ester and so on. They may have the completely same chemical structures, or totally different chemical structures, or some of them have the same chemical structures and the others have the different chemical structures. PEG is the chain segment consisting of repeated unit $CH_2CH_2O$, with a molecular weight from 100 to 1,000,000.

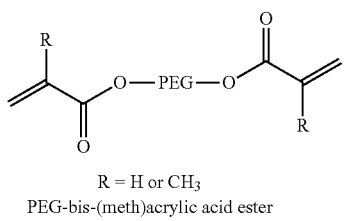

R = H or $CH_3$
PEG-bis-(meth)acrylic acid ester

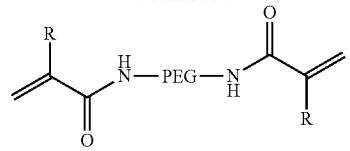

R = H or CH₃
PEG-bis-(meth)acrylamide

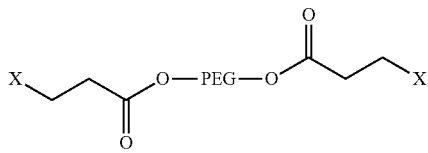

X = I, Br or Cl
PEG-bis-halogenated propionic acid ester

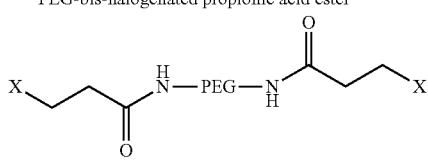

X = I, Br or Cl
PEG-bis-halogenated propionamide

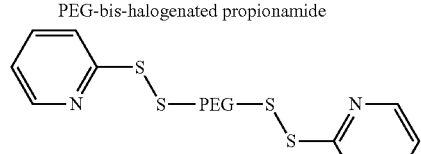

PEG-bis-dipyridyl disulfide

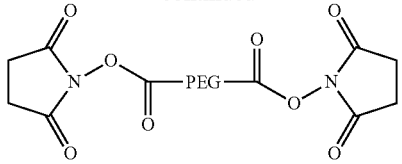

PEG-bis-N-hydroxysuccinimide

The usual method for preparing cross-linked materials composed of the thiol-modified macromolecule derivatives of this invention and cross-linked by thiol-reactive crosslinker, is as follows: prepare the aqueous solution or mixed aqueous solution contained one or more thiol-modified macromolecule derivatives with general formula (I) or (II), adjust the pH value of the above solution to neutral, then add in the aqueous solution of above thiol-reactive crosslinker, mix uniformly, the gel will form after keep standing for a moment at room temperature and the crosslinking material is formed. The thiols of the thiol-modified macromolecule derivatives with general formula (I) of this invention are more active and react with crosslinker more rapidly. However, the thiols of the thiol-modified macromolecule derivatives with general formula (I) of this invention are more stable and react with crosslinker more slowly.

The thiol-modified macromolecule derivatives with general formula (I) in this invention and the above-mentioned two-arm PEG thiol-reactive crosslinker are taken as examples to illustrate the structures of cross-linked materials composed of one or two thiol-modified macromolecule derivatives and cross-linked by thiol-reactive crosslinker as follows:

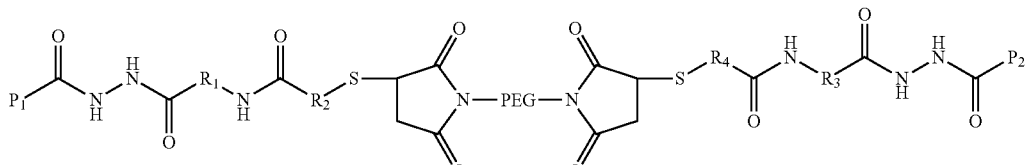

crosslinked by PEG-bis-maleimide

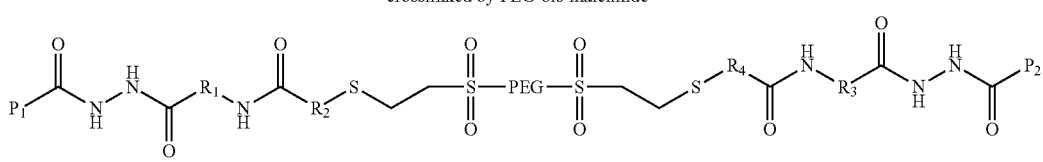

crosslinked by PEG-bis-vinyl sulfone

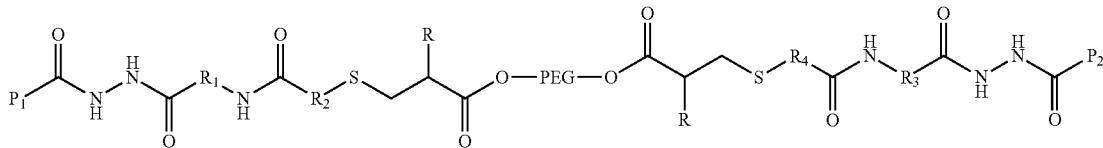

R = H or CH₃
crosslinked by PEG-bis-(meth)acrylic acid ester

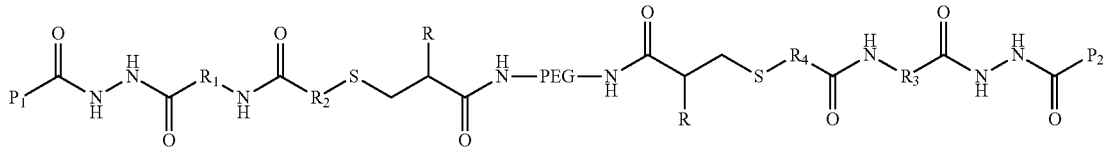

R = H or CH₃
crosslinked by PEG-bis-(meth)acrylamide

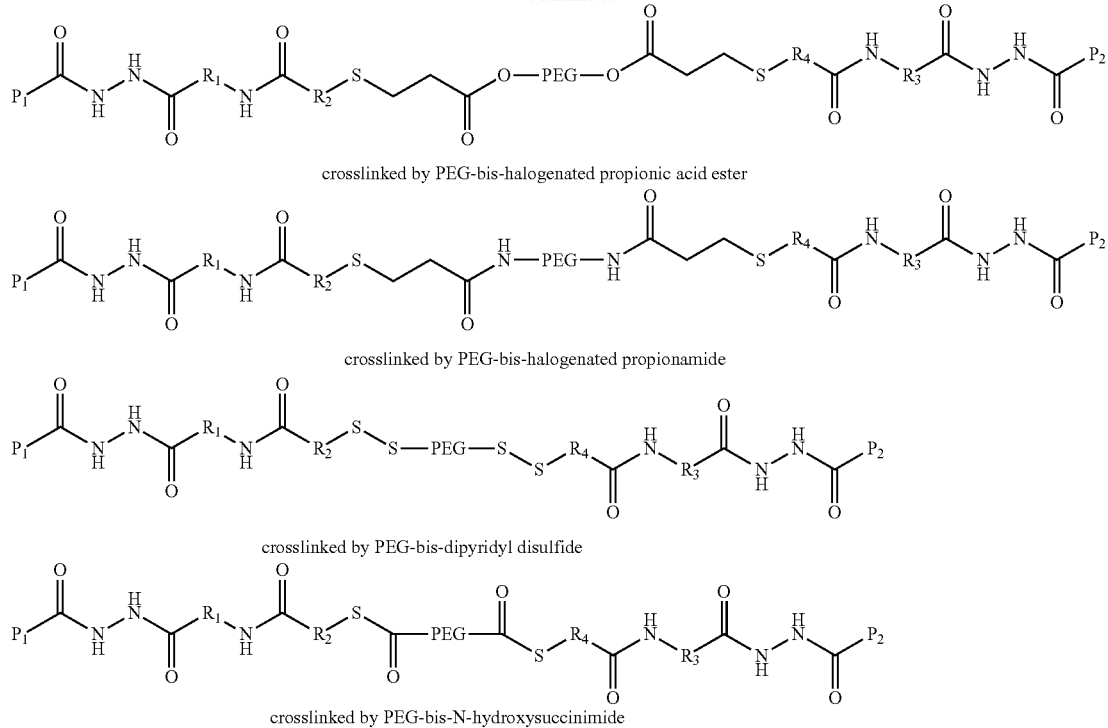

crosslinked by PEG-bis-halogenated propionic acid ester crosslinked by PEG-bis-halogenated propionamide crosslinked by PEG-bis-dipyridyl disulfide crosslinked by PEG-bis-N-hydroxysuccinimide Wherein, $P_1$ and $P_2$ are the residues of macromolecules with side carboxyl groups, defined as previously; $R_1$, $R_2$, $R_5$ and $R_4$ are also defined as previously; $R_1$, $R_2$, $R_5$ and $R_4$ may have same or different chemical structures. It is the single-component cross-linked material while $P_1$ is same as $P_2$ and it is the two-component cross-linked material while $P_1$ is not same as $P_2$. The cross-linked material composed of thiol-modified macromolecule derivatives and cross-linked by thiol-reactive crosslinker, can also be prepared through co-cross-linked with two or more above-mentioned two-arm PEG thiol-reactive crosslinker. In addition, the cross-linked material composed of thiol-modified macromolecule derivatives and cross-linked by thiol-reactive crosslinker, can also be prepared using one or more multi-arm PEG derivative crosslinker (such as three-arm PEG derivative crosslinker, four-arm PEG derivative crosslinker, eight-arm PEG derivative crosslinker and so on). The cross-linked material composed of thiol-modified macromolecule derivatives with general formula (II) and (I) and cross-linked by thiol-reactive crosslinker have the analogous structures.

The cross-linked material composed of three or more thiol-modified macromolecule derivatives and cross-linked by thiol-reactive crosslinker, can be prepared using three or more thiol-modified macromolecule derivatives with general formula (I) or (II) of this invention. The usual preparing route is as follows: firstly prepare the mixed solution of three or more thiol-modified macromolecule derivative with general formula (I) or (II), then adjust the pH value of the solution to neutral and add in one or more above-mentioned PEG thiol-reactive crosslinkers, thus to prepare multi-component cross-linked materials.

THE BEST MODE TO REALIZE THE INVENTION

Figure 1:
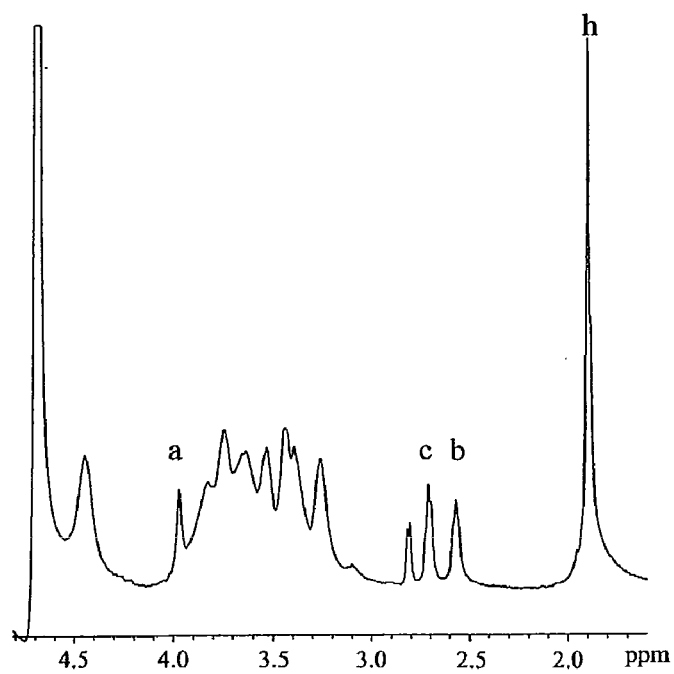
FIG. 1 is the picture of hydrogen nuclear magnetic resonance spectrum and the major chemical shift peak assignment of the derivative with low substitution degree in Example 4 of this invention ($D_2O$ is used as the solvent)

The following examples may allow the technician in this field to understand the invention more comprehensively, but not form restriction on the invention in any way.

Example 1

Synthesis of Dithiodiethanediyldicarbonyldiamino Diacetic Acid Dihydrazide (Abbr. DGDTPDH)

In a 1000 ml beaker, 10 g of dithiodipropionic acid (Aldrich, USA) and 50 ml of anhydrous dimethyl formamide is added and dissolved under stirring at room temperature, then 17.0 g of carbonyldiimidazole (Aldrich, USA) is added into above solution, a lot of $CO_2$ bubbles and white precipitate form in the solution. The reaction is conducted for 3 hours under reduced pressure at room temperature. Then 14.7 g of glycine ethyl ester hydrochloride (Aldrich, USA) is added into above solution, stirring for 1 hour. After that 500 ml of ethyl ether is added, keep standing for 1 hour, then the organic phase at upper layer is poured with caution and abandoned, 100 ml of alcohol and 10 ml of hydrazine hydrate are added, stirring overnight at room temperature. The white precipitated product is collected by filtration, rinsed twice with 200 ml of anhydrous alcohol, and dried under reduced pressure to get approximately 8.5 g of slightly yellow solid product DGDTPDH. The yield is about 50%.

Example 2

Synthesis of Thiol-Modified Hyaluronic Acid Derivative Modified by DGDTPDH with Low Substitution Degree (HA-DGDTPDH)

1 g of hyaluronate sodium (molecular weight 0.62~1.15 million, NovaMatrix FMC BIOPOLYMER, USA) is dissolved in 200 ml of distilled water to give a clear and transparent solution. 1.32 g of DGDTPDH prepared in Example 1 is added into above solution, dissolved under stirring. The solution pH is adjusted to 4.75 by adding 0.1 mol/L HCl solution, and 0.36 g of 1-ethyl-3-(3-dimethylaminopropyl) carbodiimide hydrochloride (Aldrich, USA) is added, stirring magnetically. The solution pH is maintained at 4.75 by continuously adding sufficient 0.1 mol/L HCl solution. The viscosity of the solution increases gradually, and gel forms at ca. 15 minute. After gel formation, keep still and reaction is conducted at room temperature for 2 hours. Then 10 g of dithiothreitol (Diagnostic Chemical Limited, USA) and a little of 0.1 mol/L NaOH solution are added, stirring. The gel dissolves gradually and the solution pH is maintained at 8.5 by continuously adding sufficient 0.1 mol/L NaOH solution. After dissolution of all gel, the reaction is conducted for 24 hours under magnetic stirring at room temperature. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride and the dialyzate is replaced every 8 hours. Then the dialysis is conducted for 3 days further in 10 L of 0.001 mol/L HCl solution and the dialyzate is replaced every 8 hours. At last the solution in dialysis tube is collected and freeze-dried to get approximately 0.7 g of white flocculent solid.

Example 3

Synthesis of Thiol-Modified Hyaluronic Acid Derivative Modified by DGDTPDH with High Substitution Degree (HA-DGDTPDH)

1 g of hyaluronate sodium (molecular weight 0.62~1.15 million, NovaMatrix FMC BIOPOLYMER, USA) is dissolved in 200 ml of distilled water to give a clear and transparent solution. 2.64 g of DGDTPDH prepared in Example 1 is added into above solution, dissolved under stirring. Then the solution pH is adjusted to 4.75 by adding 0.1 mol/L HCl solution, and 0.96 g of 1-ethyl-3-(3-dimethylaminopropyl) carbodiimide hydrochloride (Aldrich, USA) is added, stirring magnetically. The solution pH is maintained at 4.75 by continuously adding sufficient 0.1 mol/L HCl solution. The viscosity of the solution increases gradually, and gel comes into being at ca. 10 minute. After the formation of gel, keep still and conduct reaction at room temperature for 2 hours. Then 20 g of dithiothreitol (Diagnostic Chemical Limited, USA) and a little of 0.1 mol/L NaOH solution are added, stirring. The gel dissolves gradually and the solution pH is maintained at 8.5 by continuously adding sufficient 0.1 mol/L NaOH solution. After dissolution of all gel, the reaction is conducted for 24 hours under magnetic stirring at room temperature. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride solution and the dialyzate is replaced every 8 hours. Then the dialysis is conducted for 3 days further in 10 L of 0.001 mol/L HCl solution and the dialyzate is replaced every 8 hours. At last the solution in dialysis tube is collected and freeze-dried to get approximately 0.7 g of white flocculent solid.

Example 4

Characterization of Thiol-Modified Hyaluronic Acid Derivative Modified by DGDTPDH (HA-DGDTPDH)

The chemical structure of Ha-DGDTPDH is as follows:

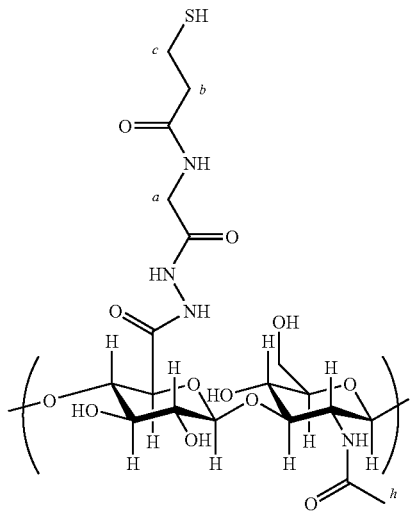

The characterization of HA-DGDTPDH prepared in Example 2 and Example 3 is as follows:

1. No small molecular impurity peak is detected using Gel Permeation Chromatography (GPC, pure water is used as the mobile phase, measure the absorption at 210 nm of ultraviolet light), which indicates that the HA-DGDTPDH with low substitution degree prepared in Example 2 and the HA-DGDTPDH with high substitution degree prepared in Example 3 have been highly purified and the impurity can not be detected by the instrument.

Figure 2:
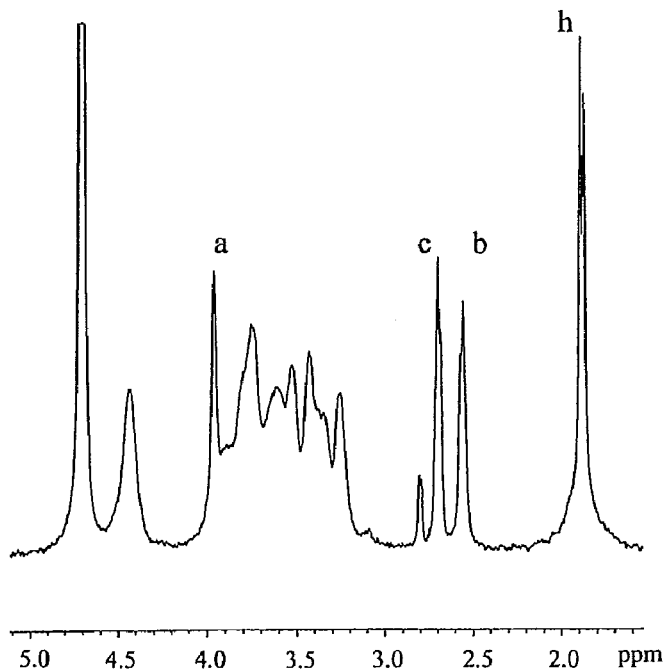
FIG. 2 is the picture of hydrogen nuclear magnetic resonance spectrum and the major chemical shift peak assignment of the derivative with high substitution degree in Example 4 of this invention ($D_2O$ is used as the solvent)
Figure 3:
FIG. 3 is the morphologic picture of cells cultured on the surface of blank cell culture pate in Example 20 of this invention.
Figure 4:
FIG. 4 is the morphologic picture of cells cultured on the surface of hyaluronic acid-gelatin hydrogel cross-linked by PEG-bis-acrylic acid ester in Example 20 of this invention.

2. Detection using hydrogen nuclear magnetic resonance ($^1$H-NMR, $D_2O$ is used as the solvent). The spectrum and chemical shift peak assignment are shown in FIG. 1 and FIG. 2. Three new absorption peaks of HA-DGDTPDH appear at δ3.96, 2.70, 2.56 ppm, which correspond to hydrogen absorptions of three methylenes in side chains of $CH_2NHC(O)$ $CH_2CH_2SH$, $CH_2NHC(O)CH_2CH_2SH$, $CH_2NHC(O)$ $CH_2CH_2SH$. The small absorption peak, whose chemical shift is about δ 2.8 ppm, represents a little product of side reaction.

The characteristic absorption peak of methyl in acetyl of hyaluronic acid is taken as internal standard to figure out the substitution degree of HA-DGDTPDH which is low in Example 2 (27%) and high in Example 3 (59%) based on the area of absorption peaks.

3. Measurement of molecular weight and its distribution (measured using GPC, monodisperse hyaluronic acid is used to adjust the standard curve): as to HA-DGDTPDH with low substitution degree prepared in Example 2, the weight-average molecular weight ($M_w$) is 1,020,000 and the number-average molecular weight ($M_n$) is 530,000 and the molecular weight distribution is 1.92; as to HA-DGDTPDH with high substitution degree prepared in Example 3, the weight-average molecular weight ($M_w$) is 1,230,000 and the number-average molecular weight ($M_n$) is 580,000 and the molecular weight distribution is 2.12.

4. The content of active thiol of HA-DGDTPDH prepared in Example 2 and Example 3 is measured using improved Ellman method reported in *Biomacromolecules*, 3, 1304, 2002 by Shu et al. The content of active thiol in side chains of HA-DGDTPDH with low substitution degree prepared in Example 2 is 25.4 thiol per 100 repeated units of disaccharide in hyaluronic acid. The content of active thiol in side chains of HA-DGDTPDH with high substitution degree prepared in Example 3 is 55.1 thiol per 100 repeated units of disaccharide in hyaluronic acid. The results are almost consistent with the data detected using hydrogen nuclear magnetic resonance.

Example 5

Synthesis of Dithiodiethanediyldicarbonyldiamino Dipropionic Acid Dihydrazide (Abbr. DPDTPDH)

In a 1000 ml beaker, 10 g of dithiodipropionic acid (Aldrich, USA) and 50 ml of anhydrous dimethyl formamide are added and dissolved under stirring at room temperature, 17.0 g of carbonyldiimidazole (Aldrich, USA) is added into above solution, a lot of $CO_2$ bubbles and white precipitate are generated in the solution. The reaction is conducted for 3 hours under reduced pressure at room temperature. Then 14.7 g of aminopropionic acid ethyl ester hydrochloride (Aldrich, USA) is added into above solution, stirred for 1 hour. After 500 ml ethyl ether is added, keep stand for 1 hour, the organic phase at upper layer is poured with caution and abandoned. Then 100 ml of alcohol and 10 ml of hydrazine hydrate are added, stirred overnight at room temperature. The white precipitated product is collected by filtration, rinsed twice with 200 ml of anhydrous alcohol, and dried under reduced pressure to get approximately 7.3 g of slightly yellow solid product DPDTPDH. The yield is about 40%.

Example 6

Synthesis and Characterization of Thiol-Modified Hyaluronic Acid Derivative Modified by DPDTPDH (HA-DPDTPDH)

1 g of hyaluronate sodium (molecular weight 0.62~1.15 million, NovaMatrix FMC BIOPOLYMER, USA) is dissolved in 200 ml of distilled water to give a clear and transparent solution. 1.43 g of DPDTPDH prepared in Example 5 is added into above solution, dissolved under stirring. Then the solution pH is adjusted to 4.75 by adding 0.1 mol/L HCl solution, and 0.48 g of 1-ethyl-3-(3-dimethylaminopropyl)carbodiimide hydrochloride (Aldrich, USA) is added, stirring magnetically. The solution pH is maintained at 4.75 by continuously adding sufficient 0.1 mol/L HCl solution. The viscosity of the solution increases gradually, and gel forms at ca. 15 minute. After the formation of gel, keep still and conduct reaction at room temperature for 2 hours. Then 12 g of dithiothreitol (Diagnostic Chemical Limited, USA) and a little of 0.1 mol/L NaOH solution are added, stirring. The gel dissolves gradually and the solution pH is maintained at 8.5 by continuously adding sufficient 0.1 mol/L NaOH solution. After dissolution of all gel, the reaction is conducted for 24 hours under magnetic stirring at room temperature. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride and the dialyzate is replaced every 8 hours. Then the dialysis is conducted for 3 days further in 10 L of 0.001 mol/L HCl solution and the dialyzate is replaced every 8 hours. At last the solution in dialysis tube is collected and freeze-dried to get approximately 0.7 g of white flocculent solid.

No small molecular impurity peak is detected using GPC (pure water is used as the mobile phase, measure the absorption at 210 nm of ultraviolet light), which indicates that the synthesized HA-DPDTPDH has been highly purified and the impurity can not be detected by the instrument.

Detected using hydrogen nuclear magnetic resonance ($^1$H-NMR, $D_2O$ is used as the solvent). Two new absorption peaks of HA-DPDTPDH appear at δ 3.4, 2.66 ppm, which correspond to hydrogen absorptions of two methylenes in side chains of $CH_2CH_2NHC(O)CH_2CH_2SH$ and $CH_2CH_2NHC(O)CH_2CH_2SH$. Hydrogen absorption peak of methylene in side chain of $CH_2CH_2NHC(O)CH_2CH_2SH$ is overlapped with one of $CH_2CH_2NHC(O)CH_2CH_2SH$ at δ 2.5 ppm. The small absorption peak, whose chemical shift is about δ 2.8 ppm, represents a little product of side reaction.

The characteristic absorption peak of methyl in acetyl of hyaluronic acid is taken as internal standard to figure out that substitution degree of side chain in the synthesized HA-DPDTPDH is 61% based on the area of absorption peaks.

Measurement of molecular weight and its distribution (measured using GPC, monodisperse hyaluronic acid is used to adjust the standard curve): the weight-average molecular weight ($M_w$) is 1,220,000 and the number-average molecular weight ($M_n$) is 670,000 and the molecular weight distribution is 1.82.

The content of active thiol of HA-DPDTPDH measured using improved Ellman method reported in *Biomacromolecules*, 3, 1304, 2002 by Shu et al. is 53.6 thiol per 100 repeated units of disaccharide in hyaluronic acid. The result is slightly lower than that of detecting using hydrogen nuclear magnetic resonance.

Example 7

Synthesis of Dithiodiethanediyldiaminodicarbonyl Dipropionic Acid Dihydrazide (Abbr. DSCDH)

100 g of cystamine dihydrochloride (Aldrich, USA) is dissolved into 1500 ml of distilled water to give a clear and transparent solution. Sufficient 4 mol/L NaOH solution is added until the pH is 10. Then under magnetic stirring, 133 g of succinic anhydride (Aldrich, USA) is added, and simultaneously the solution pH is maintained at 7~10 by continuously adding sufficient 4 mol/L NaOH. After reaction for 2 hours at room temperature, 6 mol/L HCl is added into the solution, the white precipitated product is collected by filtration, washed twice with 2000 ml distilled water, dried under reduced pressure to get approximately 150 g of white solid product dithiodiethanediyldiaminodicarbonyl dipropionic acid (abbr. DSC). The yield is higher than 90%.

In a 2500 ml three-neck round-bottom flask, 100 g of DSC, 1200 ml of anhydrous alcohol and 100 drops of concentrated sulfuric acid are added. After refluxed for 2 hours under nitrogen protection, the solution is concentrated under reduced pressure to a volume less than 200 ml. Then the remained solution is transferred into a 2500 ml tap funnel, and 600 ml of ethyl acetate is added. Then the organic phase is washed with 500 ml water for three times, the aqueous phase was abandoned, and the organic phase is distilled under reduced pressure to get approximately 93 g of white lardaceous solid product dithiodiethanediyldiaminodicarbonyl dipropionic acid diethyl ester (abbr. DSCDE). The yield is higher than 80%.

In a 150 ml beaker, 10 g of DSCDE and 80 ml of alcohol are added and dissolved under stirring, then 10 ml of hydrazine hydrate (Aldrich, USA) is added. After overnight reaction, the white precipitated product is collected by filtration, and rinsed with 40 ml of alcohol for 4 times. The organic solvent is evaporated at room temperature in a fume hood, and then the product is dried under reduced pressure to get approximately 8 g of white solid DSCDH. The yield is higher than 75%.

Example 8

Synthesis and Characterization of Thiol-Modified Hyaluronic Acid Derivative Modified by DSCDH (HA-DSCDH)

1 g of hyaluronate sodium (molecular weight 0.62~1.15 million, NovaMatrix FMC BIOPOLYMER, USA) is dissolved in 200 ml of distilled water to give a clear and transparent solution. 0.95 g of DSCDH prepared in Example 7 is added into above solution, dissolved under stirring. Then the solution pH is adjusted to 4.75 by adding 0.1 mol/L HCl solution, and 0.288 g of 1-ethyl-3-(3-dimethylaminopropyl)carbodiimide hydrochloride (Aldrich, USA) is added, stirring magnetically. The solution pH is maintained at 4.75 by continuously adding sufficient 0.1 mol/L HCl solution. The viscosity of the solution increases gradually, and gel forms at ca. 10 minute. After the gel is formed, keep still and conduct reaction at room temperature for 2 hours. Then 10 g of dithiothreitol (Diagnostic Chemical Limited, USA) and a little of 0.1 mol/L NaOH solution are added, stirring. The gel dissolves gradually and simultaneously the solution pH is maintained at 8.5 by continuously adding sufficient 0.1 mol/L NaOH solution. After dissolution of all gel, the reaction is conducted for 24 hours under magnetic stirring at room temperature. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride and the dialyzate is replaced every 8 hours.

Then the dialysis is conducted for 3 days further in 10 L of 0.001 mol/L HCl solution and the dialyzate is replaced every 8 hours. At last the solution in dialysis tube is collected and freeze-dried to get approximately 0.7 g of white flocculent solid.

No small molecular impurity peak is detected using GPC (pure water is used as the mobile phase, measure the absorption at 210 nm of ultraviolet light), which indicates that the synthesized HA-DSCDH has been highly purified and the impurity can not be detected by the instrument.

Detected using hydrogen nuclear magnetic resonance ($^1$H-NMR, $D_2O$ is used as the solvent). Two new absorption peaks of HA-DSCDH appear at δ 3.26, 2.5 ppm. Wherein, the peak at δ 3.26 corresponds to hydrogen absorption of the methylene in side chain of $CH_2CH_2C(O)NHCH_2CH_2SH$. Three peaks of hydrogen absorption of methylene in side chains of $CH_2CH_2C(O)NHCH_2CH_2SH$, $CH_2CH_2C(O)NHCH_2CH_2SH$ and $CH_2CH_2C(O)NHCH_2CH_2SH$ are overlapped at δ 2.5 ppm.

The characteristic absorption peak of methyl in acetyl of hyaluronic acid is taken as internal standard to figure out that the substitution degree of side chain in the synthesized HA-DSCDH is 38% based on the area of absorption peaks.

The content of active thiol of HA-DSCDH measured using improved Ellman method reported in *Biomacromolecules*, 3, 1304, 2002 by Shu et al. is 39.1 thiol per 100 repeated units of disaccharide in hyaluronic acid. The result is almost consistent with of the data detected using hydrogen nuclear magnetic resonance.

Example 9

Synthesis and Characterization of Thiol-Modified Chondroitin Sulfate Derivative Modified by DSCDH (CS-DSCDH)

1 g of chondroitin sulfate (C form, from shark cartilage, Sigma, USA) is dissolved in 100 ml of distilled water to give a clear and transparent solution. 0.704 g of DSCDH prepared in Example 7 is added into above solution, dissolved under stirring. Then the solution pH is adjusted to 4.75 by adding 0.1 mol/L HCl solution, and 0.192 g of 1-ethyl-3-(3-dimethylaminopropyl)carbodiimide hydrochloride (Aldrich, USA) is added, stirring magnetically. The solution pH is maintained at 4.75 by continuously adding sufficient 0.1 mol/L HCl solution, and the reaction is conducted 2 hours under magnetic stirring at room temperature. Then 10 g of dithiothreitol (Diagnostic Chemical Limited, USA) and a little of 0.1 mol/L NaOH solution are added, stirring. The gel dissolves gradually and simultaneously the solution pH is maintained at 8.5 by continuously adding sufficient 0.1 mol/L NaOH solution. After dissolution of all gel, the reaction is conducted for 24 hours under magnetic stirring at room temperature. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride and the dialyzate is replaced per 8 hours. Then the dialysis is conducted for 3 days further in 10 L of 0.001 mol/L HCl solution and the dialyzate is replaced per 8 hours. At last the solution in dialysis tube is collected and freeze-dried to get approximately 0.6 g of white flocculent solid.

No small molecular impurity peak is detected using GPC (pure water is used as the mobile phase, measure the absorption at 210 nm of ultraviolet light), which indicates that the synthesized CS-DSCDH has been highly purified and the impurity can not be detected by the instrument.

Detected using hydrogen nuclear magnetic resonance ($^1$H-NMR, $D_2O$ is used as the solvent). Two new absorption peaks of CS-DSCDH appear at δ 3.27, 2.54 ppm. Wherein, the peak at δ 3.27 corresponds to hydrogen absorption of the methylene in side chain of $CH_2CH_2C(O)NHCH_2CH_2SH$. Three peaks of hydrogen absorption of methylene in side chains of $CH_2CH_2C(O)NHCH_2CH_2SH$, $CH_2CH_2C(O)NHCH_2CH_2SH$ and $CH_2CH_2C(O)NHCH_2CH_2SH$ are overlapped at δ 2.54 ppm.

The characteristic absorption peak of methyl in acetyl of hyaluronic acid is taken as internal standard to figure out that the substitution degree of side chain in synthesized CS-DSCDH is 47% based on the area of absorption peaks.

Measurement of molecular weight and its distribution (measured using GPC, monodisperse hyaluronic acid is used to adjust the standard curve): the weight-average molecular weight ($M_w$) is 38,000 and the number-average molecular weight ($M_n$) is 17,000 and the molecular weight distribution is 2.23.

The content of active thiol of CS-DSCDH measured using improved Ellman method reported in *Biomacromolecules*, 3, 1304, 2002 by Shu et al. is 44.2 thiol per 100 repeated units of disaccharide in hyaluronic acid. The result is slightly lower than that detected using hydrogen nuclear magnetic resonance.

Example 10

Synthesis and Characterization of Thiol-Modified Gelatin Derivative Modified by DSCDH (GEL-DSCDH)

1 g of gelatin (type B, from pig skin, Sigma, USA) is dissolved in 100 ml of distilled water to give a clear and transparent solution. 0.75 g of DSCDH prepared in Example 7 is added into above solution, dissolved under stirring. Then the solution pH is adjusted to 4.75 by adding 0.1 mol/L HCl solution, and 1 g of 1-ethyl-3-(3-dimethylaminopropyl)carbodiimide hydrochloride (Aldrich, USA) is added, stirring magnetically. The solution pH is maintained at 4.75 by continuously adding sufficient 0.1 mol/L HCl solution, and reaction is conducted at room temperature for 2 hours. Then 10 g of dithiothreitol (Diagnostic Chemical Limited, USA) and a little of 0.1 mol/L NaOH solution are added until pH 8.5. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride and the dialyzate is replaced per 8 hours. Then the dialysis is conducted for 3 days further in 10 L of 0.001 mol/L HCl solution and the dialyzate is replaced per 8 hours. At last the solution in dialysis tube is collected and freeze-dried to get approximately 0.6 g of white flocculent solid.

No small molecular impurity peak is detected using GPC (pure water is used as the mobile phase, measure the absorption at 210 nm of ultraviolet light), which indicates that the synthesized GEL-DSCDH has been highly purified and the impurity can not be detected by the instrument.

Detected using hydrogen nuclear magnetic resonance ($^1$H-NMR, $D_2O$ is used as the solvent). Two new absorption peaks of GEL-DSCDH appear at δ 3.27, 2.51 3.28, 2.53 ppm. Wherein, the peak at δ 3.28 corresponds to hydrogen absorption of the methylene in side chain of $CH_2CH_2C(O)NHCH_2CH_2SH$. Three peaks of hydrogen absorption of methylene in side chains of $CH_2CH_2C(O)NHCH_2CH_2SH$, $CH_2CH_2C(O)NHCH_2CH_2SH$ and $CH_2CH_2C(O)NHCH_2CH_2SH$ are overlapped at δ 2.53 ppm.

Measurement of molecular weight and its distribution (measured using GPC, monodisperse hyaluronic acid is used to adjust the standard curve): the weight-average molecular weight ($M_w$) is 56,000 and the number-average molecular weight ($M_n$) is 21,000 and the molecular weight distribution is 2.67.

The content of active thiol of GEL-DSCDH measured using improved Ellman method reported in *Biomacromolecules*, 3, 1304, 2002 by Shu et al. is 0.57 mmol/L thiol per 1 g of GEL-DSCDH.

Example 11

Synthesis of Dithiodiethanediyldiaminodicarbonyl Dibutanoic Acid Dihydrazide (Abbr. DGCDH)

100 g of cystamine dihydrochloride (Aldrich, USA) is dissolved into 1500 ml of distilled water to give a clear and transparent solution. Sufficient 4 mol/L NaOH solution is added until the pH is 10. Then under magnetic stirring, 152 g of glutaric anhydride (Aldrich, USA) is added, and simultaneously the solution pH is maintained at 7~10 by continuously adding sufficient 4 mol/L NaOH. After reaction at room temperature for two hours, 6 mol/L HCl is added into the solution, the white precipitated product is collected by filtration, washed twice with 2000 ml distilled water, and then dried under reduced pressure to get approximately 155 g of white solid product dithiodiethanediyldiaminodicarbonyl dibutanoic acid (abbr. DGC). The yield is higher than 90%.

In a 2500 ml three-neck round-bottom flask, 100 g of DGC, 1200 ml of anhydrous alcohol and 100 drops of concentrated sulfuric acid are added. After refluxed for 2 hours under nitrogen protection, the solution is concentrated under reduced pressure to a volume less than 200 ml. Then the remained solution is transferred into a 2500 ml tap funnel, and 600 ml of ethyl acetate is added. Then the organic phase is washed with 500 ml water for three times and the organic phase is distilled under reduced pressure to get approximately 94 g of white lardaceous solid product dithiodiethanediyl-diaminodicarbonyl dibutanoic acid diethyl ester (abbr. DGCDE). The yield is higher than 80%.

In a 150 ml beaker, 10 g of DGCDE and 80 ml of alcohol are added and dissolved under stirring at room temperature, then 10 ml of hydrazine hydrate (Aldrich, USA) is added. After overnight reaction, the white precipitated product is collected by filtration, and rinsed with 40 ml of alcohol for four times. The organic solvent is evaporated at room temperature in a fume hood, and then the product is dried under reduced pressure to get approximately 7.1 g of white solid DGCDH. The yield is higher than 75%.

Example 12

Synthesis and Characterization of Thiol-Modified Hyaluronic Acid Derivatives Modified by DGCDH (HA-DGCDH)

1 g of hyaluronate sodium (molecular weight 0.62~1.15 million, NovaMatrix FMC BIOPOLYMER, USA) is dissolved in 200 ml of distilled water to give a clear and transparent solution. 1.53 g of DSCDH prepared in Example 11 is added into above solution, dissolved under stirring. Then the solution pH is adjusted to 4.75 by adding 0.1 mol/L HCl solution, and 0.48 g of 1-ethyl-3-(3-dimethylaminopropyl) carbodiimide hydrochloride (Aldrich, USA) is added, stirring magnetically. The solution pH is maintained at 4.75 by continuously adding sufficient 0.1 mol/L HCl solution. The viscosity of the solution increases gradually, and gel forms at ca. 10 minute. After the gel is formed, keep still and conduct reaction at room temperature for 2 hours. Then 10 g of dithiothreitol (Diagnostic Chemical Limited, USA) and a little of 0.1 mol/L NaOH solution are added, stirring. The gel dissolves gradually and simultaneously the solution pH is maintained at 8.5 by continuously adding sufficient 0.1 mol/L NaOH solution. After dissolution of all gel, the reaction is conducted for 24 hours under magnetic stirring at room temperature. Then sufficient 6 mol/L HCl solution is added until the pH is around 3.0. The above solution is placed into dialysis tube (the molecular weight cutoff is 3500, Sigma, USA). The dialysis is conducted for 5 days in 10 L water with 0.001 mol/L HCl and 0.3 mol/L sodium chloride and the dialyzate is replaced per 8 hours. Then the dialysis is conducted for 3 days further in 10 L of 0.001 mol/L HCl solution and the dialyzate is replaced per 8 hours. At last the solution in dialysis tube is collected and freeze-dried to get approximately 0.7 g of white flocculent solid.

No small molecular impurity peak is detected using GPC (pure water is used as the mobile phase, measure the absorption at 210 nm of ultraviolet light), which indicates that the synthesized HA-DGCDH has been highly purified and the impurity cannot be detected by the instrument.

Detected using hydrogen nuclear magnetic resonance ($^1$H-NMR, $D_2O$ is used as the solvent): Two new absorption peaks of HA-DSCDH appear at δ 3.23, 2.56, 2.3 ppm. Wherein, the peaks at δ 3.23, 2.56 ppm correspond to hydrogen absorption of the methylene in side chains of $CH_2CH_2CH_2C(O)NHCH_2CH_2SH$ and $CH_2CH_2CH_2C(O)NHCH_2CH_2SH$. Two peaks of hydrogen absorption of methylene in side chains of $CH_2CH_2CH_2C(O)NHCH_2CH_2SH$ and $CH_2CH_2CH_2C(O)NHCH_2CH_2SH$ are overlapped at δ 2.3 ppm. The peak of hydrogen absorption of methylene in side chain of $CH_2CH_2CH_2C(O)NHCH_2CH_2SH$ is overlapped with the characteristic absorption peak of methyl in acetyl of hyaluronic acid at δ 3.23 ppm.

The characteristic absorption peak of methyl in acetyl of hyaluronic acid is taken as internal standard to figure out that the substitution degree of side chain in synthesized HA-DGCDH is 52% based on the area of absorption peaks.

The content of active thiol of HA-DGCDH measured using improved Ellman method reported in *Biomacromolecules*, 3, 1304, 2002 by Shu et al. is 49.4 thiol per 100 repeated units of disaccharide in hyaluronic acid. The result is almost consistent with of the data detected using hydrogen nuclear magnetic resonance.

Example 13

Preparation of Single-Component Disulfide-Bond Cross-Linked Hydrogel

1. Preparation of Disulfide-Bond Cross-Linked Hydrogel of Hyaluronic Acid:

0.1 g of thiol-modified hyaluronic acid derivative (HA-DGDTPDH) prepared in Example 3 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. Then the solution is moved into a 25 ml glass beaker and kept stand at room temperature for 12 hours. The viscosity of the solution increases gradually and a gel forms.

2. Preparation of Disulfide-Bond Cross-Linked Hydrogel of Gelatin:

0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. Then the solution is moved into a 25 ml glass beaker and kept standing at room temperature for 12 hours. The viscosity of the solution increases gradually and a gel forms.

Example 14

Preparation of Multi-Component Disulfide-Bond Cross-Linked Hydrogel

1. Preparation of Two-Component Disulfide-Bond Cross-Linked Hydrogel of Hyaluronic Acid-Gelatin:

0.1 g of thiol-modified hyaluronic acid derivative (HA-DGDTPDH) prepared in Example 3 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. Then the two kinds of above solution are moved into a 50 ml glass beaker together, stirred magnetically for 10 min, keep standing at room temperature for 12 hours. The viscosity of the solution increases gradually and gel forms.

2. Preparation of Two-Component Disulfide-Bond Cross-Linked Hydrogel of Chondroitin Sulfate-Gelatin:

0.3 g of thiol-modified chondroitin sulfate derivative (CS-DSCDH) prepared in Example 9 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. Then the two above solutions are poured into a 50 ml glass beaker together, stirred magnetically for 10 min, keep standing at room temperature for 12 hours. The viscosity of the solution increases gradually and gel forms.

3. Preparation of Three-Component Disulfide-Bond Cross-Linked Hydrogel of Hyaluronic Acid-Chondroitin Sulfate-Gelatin:

0.1 g of thiol-modified hyaluronic acid derivative (HA-DGDTPDH) prepared in Example 3 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified chondroitin sulfate derivative (CS-DSCDH) prepared in Example 9 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified gelatin (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. Then the three kinds of above solution are move into a 50 ml glass beaker together, stirred magnetically for 10 min, keep standing at room temperature for 12 hours. The viscosity of the solution increases gradually and gel forms.

Example 15

Preparation of Single-Component Polyethylene Glycol-Bis-Vinylsulfone-Cross-Linked Hydrogel 1. Preparation of Peg-Bis-Vinyl Sulfone Cross-Linked Hydrogel of Hyaluronic Acid:

0.1 g of thiol-modified hyaluronic acid derivative (HA-DGDTPDH) prepared in Example 3 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.1 g of PEG-bis-vinyl sulfone (molecular weight is 3400, Nektar Therapeutics, USA) is dissolved in 2.5 ml of 0.1 mol/L phosphate buffer solution (pH 7.0) to give a clear and transparent solution. Then 2.5 ml of above PEG-bis-vinyl sulfone solution is added into 10 ml of above HA-DGDTPDH solution, stirred magnetically for 30 sec immediately, keep standing for 30 min at room temperature. The viscosity of the solution increases gradually and gel forms.

2. Preparation of Peg-Bis-Vinyl Sulfone Cross-Linked Hydrogel of Chondroitin Sulfate:

0.3 g of thiol-modified chondroitin sulfate derivative (CS-DSCDH) prepared in Example 9 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.1 g of PEG-bis-vinyl sulfone (molecular weight is 3400, Nektar Therapeutics, USA) is dissolved in 2.5 ml of 0.1 mol/L phosphate buffer solution (pH 7.0) to give a clear and transparent solution. Then 2.5 ml of above PEG-bis-vinyl sulfone solution is added into 10 ml of above CS-DSCDH solution, stirred magnetically for 30 sec immediately, keep standing for 30 min at room temperature. The viscosity of the solution increases gradually and gel forms.

3. Preparation of Peg-Bis-Vinyl Sulfone Cross-Linked Hydro Gel of Gelatin:

0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.1 g of PEG-bis-vinyl sulfone (molecular weight is 3400, Nektar Therapeutics, USA) is dissolved in 2.5 ml of 0.1 mol/L phosphate buffer solution (pH 7.0) to give a clear and transparent solution. Then 2.5 ml of above PEG-bis-vinyl sulfone solution is added into above 10 ml of GEL-DSCDH solution, stirred magnetically for 30 sec immediately, keep standing for 30 min at room temperature. The viscosity of the solution increases gradually and gel forms.

Example 16

Preparation of Multi-Component Peg-Bis-Acrylic Acid Ester Cross-Linked Hydrogel

1. Preparation of Two-Component Peg-Bis-Acrylic Acid Ester Cross-Linked Hydrogel of Hyaluronic Acid-Gelatin 0.1 g of thiol-modified hyaluronic acid derivative (HA-DGDTPDH) prepared in Example 3 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.2 g of PEG-bis-acrylic acid ester (molecular weight is 3400, Nektar Therapeutics, USA) is dissolved in 5 ml of 0.1 mol/L phosphate buffer solution (pH 7.0) to give a clear and transparent solution. Then above 10 ml of HA-DGDTPDH solution, 10 ml of GEL-DSCDH solution and 5 ml of PEG-bis-acrylic acid ester solution are poured into a 50 ml glass beaker together, stirred magnetically for 30 sec immediately, keep standing for 30 min at room temperature. The viscosity of the solution increases gradually and gel forms.

2. Preparation of Two-Component Peg-Bis-Acrylic Acid Ester Cross-Linked Hydrogel of Chondroitin Sulfate-Gelatin 0.3 g of thiol-modified chondroitin sulfate derivative (CS-DSCDH) prepared in Example 9 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.2 g of PEG-bis-acrylic acid ester (molecular weight is 3400, Nektar Therapeutics, USA) is dissolved in 5 ml of 0.1 mol/L phosphate buffer solution (pH 7.0) to give a clear and transparent solution. Then above 10 ml of CS-DSCDH solution, 10 ml of GEL-DSCDH solution and 5 ml of PEG-bis-acrylic acid ester solution are moved into a 50 ml glass beaker together, stirred magnetically for 30 sec immediately, keep standing for 30 min at room temperature. The viscosity of the solution increases gradually and gel forms.

3. Preparation of Three-Component Peg-Bis-Acrylic Acid Ester Cross-Linked Hydrogel of Hyaluronic Acid-Chondroitin Sulfate-Gelatin 0.1 g of thiol-modified hyaluronic acid derivative (HA-DGDTPDH) prepared in Example 3 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified chondroitin sulfate derivative (CS-DSCDH) prepared in Example 9 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of thiol-modified gelatin derivative (GEL-DSCDH) prepared in Example 10 of this invention is dissolved in 10 ml of 0.1 mol/L phosphate buffer solution (pH 7.0) to give a clear and transparent solution. Sufficient 0.1 mol/L NaOH is added into above solution until the pH of solution is 7.4. 0.3 g of PEG-bis-acrylic acid ester (molecular weight is 3400, Nektar Therapeutics, USA) is dissolved in 7.5 ml of 0.1 mol/L phosphate buffer solution (pH 7.0) to give a clear and transparent solution. Then above 10 ml of HA-DGDTPDH solution, 10 ml of CS-DSCDH solution, 10 ml of GEL-DSCDH solution and 7.5 ml of PEG-bis-acrylic acid ester solution are moved into a 50 ml glass beaker together, stirred magnetically for 30 sec immediately, keep standing for 30 min at room temperature. The viscosity of the solution increases gradually and gel forms.

Example 17

Disulfide-Bond Cross-Linked Hydrogel of Hyaluronic Acid is Used for Preventing Adherence of Cells The disulfide-bond cross-linked hydrogel of hyaluronic acid is prepared in a standard 24-well cell culture plate at 1 ml per well according to Example 13. After 12 hours, the whole cell culture plate is sterilized by dipped in 75% alcohol solution for 2 hours. Then the cell culture plate is dip-washed three times with sterile normal saline. 1 ml of cell culture medium (DMEM, 10% bovine serum) and 20,000 NIH 3T3 fibroblasts are added in each well. The cell culture plate is incubated for 24 hours at 37 in $CO_2$ cell incubator. It is observed by microscope that an absolute majority of fibroblasts are suspending over the surface of disulfide-bondcross-linked hydrogel of hyaluronic acid and they cannot adhere and spread. However, in blank wells of cell culture plate, the fibroblasts adhere on the bottom and have a spindle shape. This result indicates that the disulfide-bond cross-linked hydrogel of hyaluronic acid can prevent the adherence of cells and can be used for prevention and treatment of adhesion after surgery.

Example 18

Disulfide-Bond Cross-Linked Double-Component Hydrogel of Hyaluronic Acid-Gelatin is Used as Matrix of Cellular Adherence and Growth The disulfide-bond cross-linked double-component hydrogel of hyaluronic acid-gelatin is prepared in a standard 24-well cell culture plate at 1 ml per well according to Example 14. After 12 hours, the whole cell culture plate is sterilized by dipped in 75% alcohol solution for 2 hours. Then the cell culture plate is dip-washed three times with sterile normal saline. 1 ml of cell culture medium (DMEM, 10% bovine serum) and 20,000 NIH 3T3 fibroblasts are added in each well. The cell culture plate is incubated for 24 hours at 37□ $CO_2$ cell incubator. It is observed by microscope that the adherence and spread of cells on the surface of disulfide-bond cross-linked double-component hydrogel of hyaluronic acid-gelatin is similar with blank cell culture plate and the cells have a spindle shape. This result indicates that the disulfide-bond cross-linked two-component hydrogel of hyaluronic acid-gelatin is a good matrix of cellular adherence and growth.

Example 19

The PEG-Bis-Vinyl Sulfone Cross-Linked Hydrogel of Hyaluronic Acid is Used for Preventing Adherence of Cells The PEG-bis-vinyl sulfone cross-linked hydrogel of hyaluronic acid is prepared in a standard 24-well cell culture plate at 1 ml per well according to Example 15. After 12 hours, the whole cell culture plate is sterilized by dipped in 75% alcohol solution for 2 hours. Then the cell culture plate is dip-washed three times with sterile normal saline. 1 ml of cell culture medium (DMEM, 10% bovine serum) and 20,000 NIH 3T3 fibroblasts are added in each well. The cell culture plate is incubated for 24 hours at 37° C. in $CO_2$ cell incubator. It is observed by microscope that an absolute majority of fibroblasts are suspending over the surface of PEG-bis-vinyl sulfone cross-linked hydrogel of hyaluronic acid and they cannot adhere and spread. However, in blank wells of cell culture plate, the fibroblasts adhere on the bottom and have a spindle shape. This result indicates that the PEG-bis-vinyl sulfone cross-linked hydrogel of hyaluronic acid can prevent the adherence of cells.

Example 20

Two-Component PEG-Bis-Acrylic Acid Ester Cross-Linked Hydrogel of Hyaluronic Acid-Gelatin is Used as Matrix of Cellular Adherence and Growth The two-component PEG-his-acrylic acid ester cross-linked hydrogel of hyaluronic acid-gelatin is prepared in a standard 24-well cell culture plate at 1 ml per well according to Example 16. After 12 hours, the whole cell culture plate is sterilized by dipped in 75% alcohol solution for 2 hours. Then the cell culture plate is dip-washed three times with sterile normal saline. 1 ml of cell culture medium (DMEM, 10% bovine serum) and 20,000 NIH 3T3 fibroblasts are added in each well. The cell culture plate is incubated for 24 hours at 37□ in $CO_2$ cell incubator. It is observed by microscope that the adherence and spread of cells on the surface of two-component PEG-bis-acrylic acid ester cross-linked hydrogel of hyaluronic acid-gelatin is similar with blank cell culture plate and the cells have a spindle shape. This result indicates that the two-component PEG bis-acrylic acid ester cross-linked hydrogel of hyaluronic acid-gelatin is a good matrix of adherence and growth of cells.

INDUSTRIAL PRACTICALITY

The thiol-modified macromolecule derivatives with general formula (I) or (II) in this invention has many beneficial effects. The use of hydrazide coupling method for thiolated modification in this invention has the notable benefits of mild preparing conditions, high rate of production, high degree of modification, good controllability and so on.

Various disulfide-bond cross-linked macromolecule materials can be easily prepared according to this invention, such as the disulfide-bond cross-linked material composed of a polysaccharide, the disulfide-bond cross-linked material composed of a protein, the disulfide-bond cross-linked material composed of two polysaccharides, the disulfide-bond cross-linked material composed of two proteins, the disulfide-bond cross-linked material composed of a polysaccharide and a protein and so on. These disulfide-bond cross-linked materials can be made into film, sponge, gel and other forms and can be used to prevent the adherence of cells or used as the matrix of cellular growth.

In general, the crosslinking process between thiol-reactive crosslinker and thiol-modified macromolecule derivative with general formula (I) or (II) of this invention is very rapid, the gelation rate improves more than five times than the disulfide bond crosslinking. These materials have important uses in biomedicine, such as for embedding of cells in situ and so on. Various thiol-reactive crosslinker cross-linked macromolecular materials can be easily prepared according to this invention, such as cross-linked material composed of a polysaccharide, cross-linked material composed of a protein, cross-linked material composed of two polysaccharides, cross-linked material composed of two proteins, cross-linked material composed of a polysaccharide and a protein and so on. These thiol-reactive crosslinker cross-linked macromolecular materials can be made into film, sponge, gel and other forms and can be used to prevent the adherence of cells or used as the matrix of cellular growth.

The invention claimed is:

1. Thiol-modified macromolecule derivatives having the general formula (I) or (II):

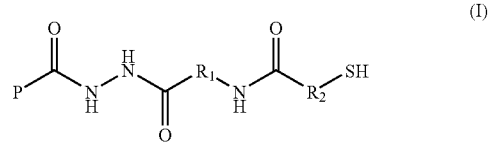

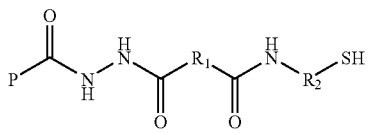

(II)

Wherein, $R_1$ and $R_2$ can be an alkylene group, a substituted alkylene group, an arylene group, a polyether backbone etc.; P is the residue of macromolecule with side carboxyl groups; said thiolated macromolecular derivatives have the molecular weight from 1000 to 5,000,000.

2. The thiol-modified macromolecule derivatives of claim 1, wherein said macromolecule with side carboxyl groups is selected from the group consisting of polysaccharide, protein and synthesized macromolecule.

3. The thiol-modified macromolecule derivatives of claim 2, wherein said polysaccharide is selected from the group consisting of chondroitin sulfate, dermatan, heparin, heparan, alginic acid, hyaluronic acid, dermatan sulfate, pectin, carboxymethyl cellulose, carboxymethyl chitosan and their salts.

4. The thiol-modified macromolecule derivatives of claim 2, wherein said synthesized macromolecule is selected from the group consisting of polyacrylic acid, polyaspartic acid, polytartaric acid, polyglutamic acid, polyfumaric acid and their salts.

5. The thiol-modified macromolecule derivatives of claim 2, wherein said protein is selected from the group consisting of collagen protein, alkaline type gelatin, acidic type gelatin, alkaline type gene-recombinated gelatin, acidic type gene-recombinated gelatin, elastin, decorin, laminin and fibronectin.

6. The thiol-modified macromolecule derivatives of claim 1, wherein $R_1$ and $R_2$ are an alkylene group respectively.

7. The thiol-modified macromolecule derivatives of claim 6, wherein $R_1$ and $R_2$ are an alkylene group having 1~8 carbon atoms respectively.

8. Disulfide-bond cross-linked macromolecule materials composed of one or more thiol-modified macromolecule derivatives of claim 1.

9. Cross-linked macromolecule materials composed of one or more thiol-modified macromolecule derivatives of claim 1 and cross-linked by crosslinker having at least two same or different thiol-reactive functional groups.

10. The cross-linked macromolecule materials of claim 9, wherein said crosslinker is selected from the group consisting of two-arm, three-arm and more arms PEG derivative having thiol-reactive functional groups and the PEG derivative has the molecular weight from 100 to 1,000,000.

11. The cross-linked macromolecule materials of claim 10, wherein said thiol-reactive functional groups is selected from the group consisting of maleimide, vinyl sulfone, α, β unsaturated acrylic acid ester, α, β unsaturated methacrylic acid ester, halogenated propionic acid ester, halogenated propionamide, dipyridyl disulfide, N-hydroxysuccinimide ester.

12. Disulfide-bond cross-linked macromolecule materials composed of one or more thiol-modified macromolecule derivatives of claim 2.

13. Disulfide-bond cross-linked macromolecule materials composed of one or more thiol-modified macromolecule derivatives of claim 3.

14. Disulfide-bond cross-linked macromolecule materials composed of one or more thiol-modified macromolecule derivatives of claim 4.

15. Disulfide-bond cross-linked macromolecule materials composed of one or more thiol-modified macromolecule derivatives of claim 5.

16. Disulfide-bond cross-linked macromolecule materials composed of one or more thiol-modified macromolecule derivatives of claim 6.

17. Disulfide-bond cross-linked macromolecule materials composed of one or more thiol-modified macromolecule derivatives of claim 7.

18. Cross-linked macromolecule materials composed of one or more thiol-modified macromolecule derivatives of claim 2 and cross-linked by crosslinker having at least two same or different thiol-reactive functional groups.

19. Cross-linked macromolecule materials composed of one or more thiol-modified macromolecule derivatives of claim 3 and cross-linked by crosslinker having at least two same or different thiol-reactive functional groups.

20. Cross-linked macromolecule materials composed of one or more thiol-modified macromolecule derivatives of claim 4 and cross-linked by crosslinker having at least two same or different thiol-reactive functional groups.

* * * * *